(12) United States Patent
Yeung et al.

(10) Patent No.: US 7,998,951 B2
(45) Date of Patent: Aug. 16, 2011

(54) HCV NS5B INHIBITORS

(75) Inventors: Kap-Sun Yeung, Madison, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 616 days.

(21) Appl. No.: 12/041,072

(22) Filed: Mar. 3, 2008

(65) Prior Publication Data
US 2008/0221090 A1    Sep. 11, 2008

Related U.S. Application Data

(60) Provisional application No. 60/892,905, filed on Mar. 5, 2007.

(51) Int. Cl.
| | |
|---|---|
| *A61P 31/00* | (2006.01) |
| *A61K 31/553* | (2006.01) |
| *A61K 31/55* | (2006.01) |
| *A61K 31/54* | (2006.01) |
| *A61K 31/535* | (2006.01) |
| *C07D 265/12* | (2006.01) |
| *C07D 267/02* | (2006.01) |
| *C07D 417/00* | (2006.01) |
| *C07D 487/00* | (2006.01) |
| *C07D 498/00* | (2006.01) |

(52) U.S. Cl. ........... 514/211.15; 514/217.05; 514/228.2; 514/230.2; 540/544; 540/599; 544/60; 544/63; 544/89; 544/101

(58) Field of Classification Search ............. 514/211.15, 514/217.05, 228.2, 230.2; 540/544, 599; 544/60, 101, 63, 89
See application file for complete search history.

(56) References Cited

U.S. PATENT DOCUMENTS

| 7,153,848 | B2 | 12/2006 | Hudyma et al. |
|---|---|---|---|
| 7,348,425 | B2 | 3/2008 | Hudyma et al. |
| 2007/0060565 | A1 | 3/2007 | Meanwell et al. |
| 2007/0078122 | A1 | 4/2007 | Bergstrom et al. |
| 2007/0184024 | A1 | 8/2007 | Meanwell et al. |
| 2007/0185083 | A1 | 8/2007 | Bergstrom et al. |
| 2007/0270405 | A1 | 11/2007 | Bender et al. |
| 2007/0270406 | A1 | 11/2007 | Gentles et al. |
| 2007/0275930 | A1 | 11/2007 | Gentles et al. |
| 2007/0275947 | A1 | 11/2007 | Bergstrom |
| 2007/0287694 | A1 | 12/2007 | Yeung et al. |

FOREIGN PATENT DOCUMENTS

| WO | WO 2005/080399 | 9/2005 |
|---|---|---|
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 12/022,541, filed Jan. 30, 2008, Kap-Sun Yeung et al.
U.S. Appl. No. 12/046,030, filed Mar. 11, 2008, Kap-Sun Yeung et al.
U.S. Appl. No. 12/039,239, filed Feb. 28, 2008, Robert G. Gentles et al.
U.S. Appl. No. 12/045,874, filed Mar. 11, 2008, Robert G. Gentles et al.
U.S. Appl. No. 12/045,766, filed Mar. 11, 2008, John A. Bender et al.
U.S. Appl. No. 12/031,844, filed Feb. 15, 2008, Andrew Nickel et al.
U.S. Appl. No. 12/046,286, filed Mar. 11, 2008, Piyasena Hewawasam et al.
U.S. Appl. No. 11/942,285, filed Nov. 19, 2007, John A. Bender et al.
U.S. Appl. No. 11/971,362, filed Jan. 9, 2008, John A. Bender et al.

*Primary Examiner* — Brenda Coleman
(74) *Attorney, Agent, or Firm* — James Epperson

(57) ABSTRACT

The invention encompasses compounds of Formula I as well as compositions and methods of using the compounds. The compounds have activity against hepatitis C virus (HCV) and are useful in treating those infected with HCV.

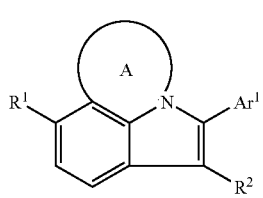

7 Claims, No Drawings

HCV NS5B INHIBITORS

CROSS-REFERENCE TO RELATED APPLICATIONS

This application claims the benefit of U.S. Provisional Application Ser. No. 60/892,905 filed Mar. 5, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

The invention encompasses compounds and pharmaceutically acceptable salts of formula I, and compositions and methods of treatment using these compounds.

One aspect of the invention is a compound of formula I

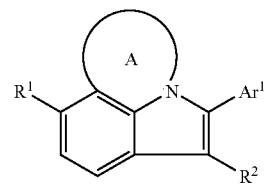

wherein:
A is a 5-7-membered ring with 1-3 heteroatoms selected from N and O and contains 0-1 double bonds, and is substituted with 0-1 substituents selected from $COR^3$ and $CONR^9R^{10}$.
$R^1$ is $CO_2R^3$ or $CONR^4R^5$;
$R^2$ is $C_{5-7}$cycloalkyl;
$R^3$ is hydrogen or alkyl;
$R^4$ is hydrogen, alkyl, cycloalkyl, $SO_2R^6$, or

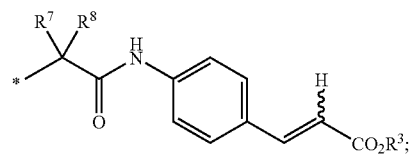

$R^5$ is hydrogen, alkyl, or cycloalkyl;
$R^6$ is alkyl, haloalkyl, cycloalkyl, amino, alkylamino, or dialkylamino;
or $R^6$ is pyrrolidinyl, piperidinyl, piperazinyl, homomorpholinyl, homopiperidinyl, morpholinyl, or thiomorpholinyl, and is substituted with 0-2 substituents selected from halo and $C_{1-6}$alkyl;
$R^7$ and $R^8$ are independently hydrogen or alkyl;
or $R^7$ and $R^8$ taken together are ethylene, propylene, butylene, pentylene, or hexalene;
$R^9$ is hydrogen, alkyl, cycloalkyl, hydroxyalkyl, (alkoxy)alkyl, aminoalkyl, (alkylamino)alkyl, or (dialkylamino)alkyl;
$R^{10}$ is hydrogen, alkyl, cycloalkyl, hydroxyalkyl, (alkoxy)alkyl, aminoalkyl, (alkylamino)alkyl, or (dialkylamino)alkyl;
or $NR^9R^{10}$ taken together is pyrrolidinyl, piperidinyl, piperazinyl, homomorpholinyl, homopiperidinyl, morpholinyl, or thiomorpholinyl, and is substituted with 0-2 substituents selected from halo, hydroxy, alkyl, amino, alkylamino, dialkylamino, pyridinyl, pyrrolidinyl, piperidinyl, piperazinyl, N-(alkyl)piperazinyl, morpholinyl, and thiomorpholinyl;
$Ar^1$ is phenyl substituted with 0-2 substituents selected from halo, alkyl, and alkoxy; and
or a pharmaceutically acceptable salt thereof.

Another aspect of the invention is a compound of formula I where the variables are as defined above and the compound is selected from the group consisting of

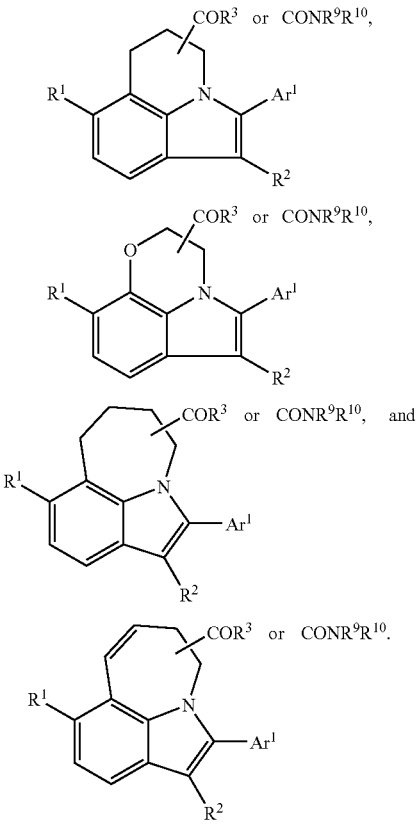

Another aspect of the invention is a compound of formula I where the variables are as defined above and the compound is selected from the group consisting of

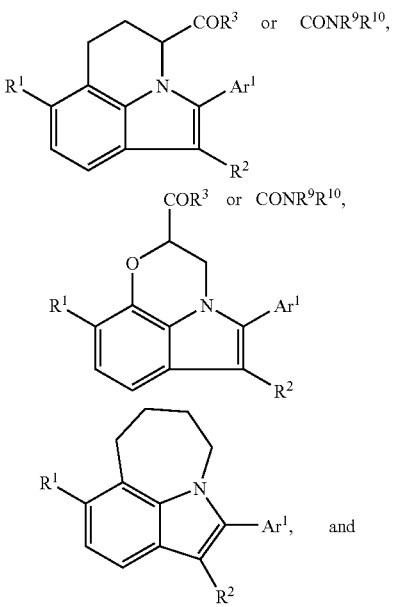

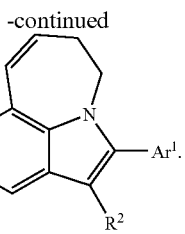

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods known in the art.

Synthetic Methods

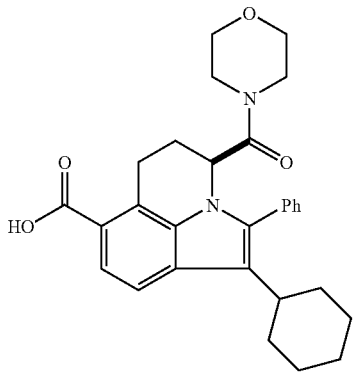

-continued

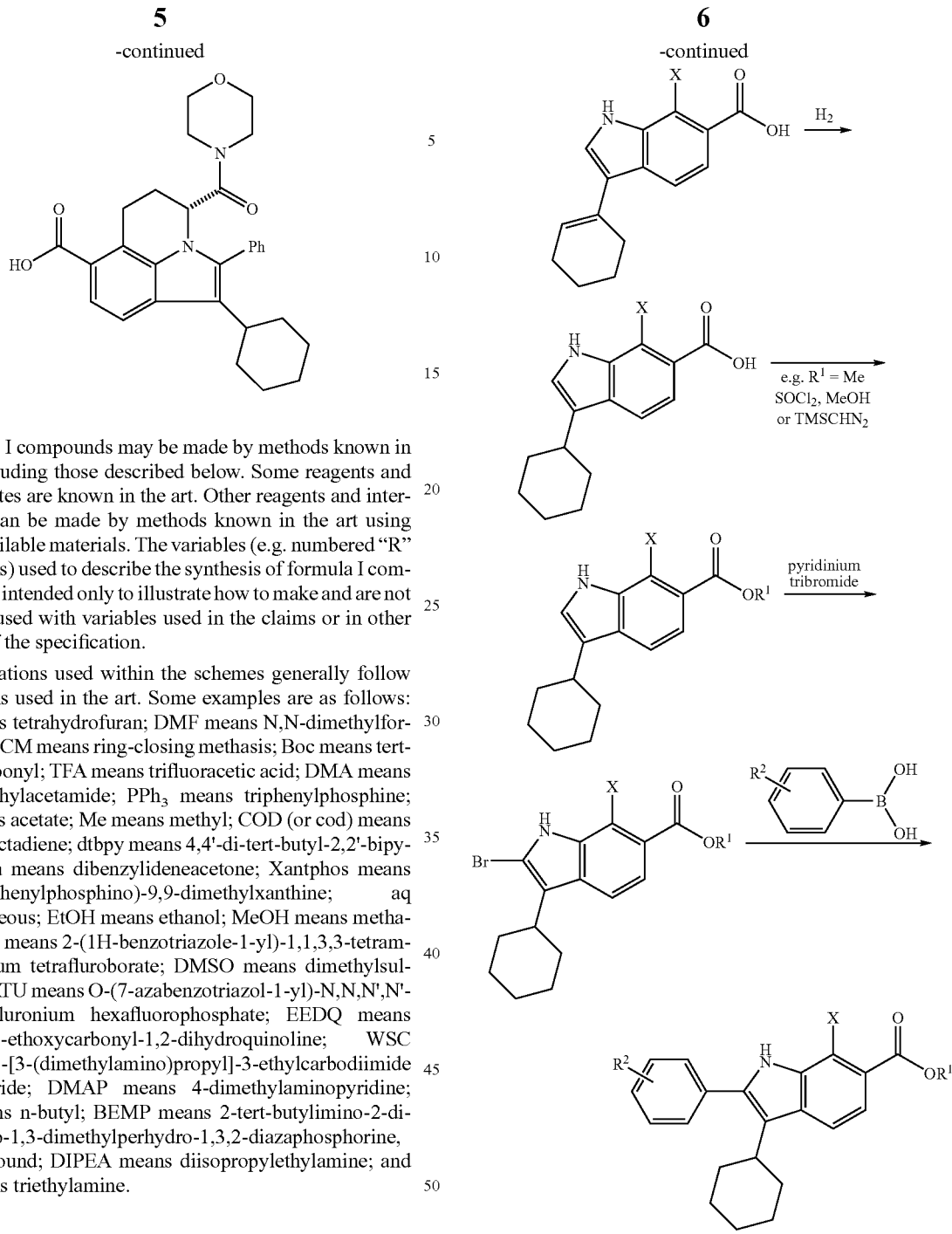

Formula I compounds may be made by methods known in the art including those described below. Some reagents and intermediates are known in the art. Other reagents and intermediates can be made by methods known in the art using readily available materials. The variables (e.g. numbered "R" substituents) used to describe the synthesis of formula I compounds are intended only to illustrate how to make and are not to be confused with variables used in the claims or in other sections of the specification.

Abbreviations used within the schemes generally follow conventions used in the art. Some examples are as follows: THF means tetrahydrofuran; DMF means N,N-dimethylformamide; RCM means ring-closing methasis; Boc means tert-butoxycarbonyl; TFA means trifluoracetic acid; DMA means N,N-dimethylacetamide; $PPh_3$ means triphenylphosphine; OAc means acetate; Me means methyl; COD (or cod) means 1,5-cyclooctadiene; dtbpy means 4,4'-di-tert-butyl-2,2'-bipyridine; dba means dibenzylideneacetone; Xantphos means 4,5-bis(diphenylphosphino)-9,9-dimethylxanthine; aq means aqueous; EtOH means ethanol; MeOH means methanol; TBTU means 2-(1H-benzotriazole-1-yl)-1,1,3,3-tetramethyluronium tetrafluroborate; DMSO means dimethylsulfoxide; HATU means O-(7-azabenzotriazol-1-yl)-N,N,N',N'-tetramethyluronium hexafluorophosphate; EEDQ means 2-ethoxy-1-ethoxycarbonyl-1,2-dihydroquinoline; WSC means 1-[3-(dimethylamino)propyl]-3-ethylcarbodiimide hydrochloride; DMAP means 4-dimethylaminopyridine; n-Bu means n-butyl; BEMP means 2-tert-butylimino-2-diethylamino-1,3-dimethylperhydro-1,3,2-diazaphosphorine, polymer-bound; DIPEA means diisopropylethylamine; and TEA means triethylamine.

Scheme 1.

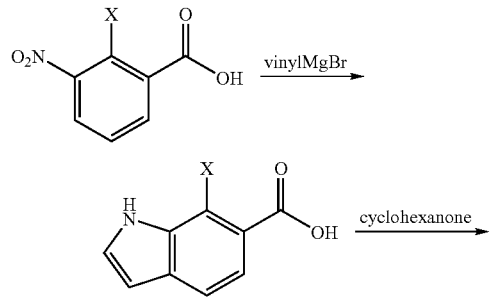

Scheme 2.

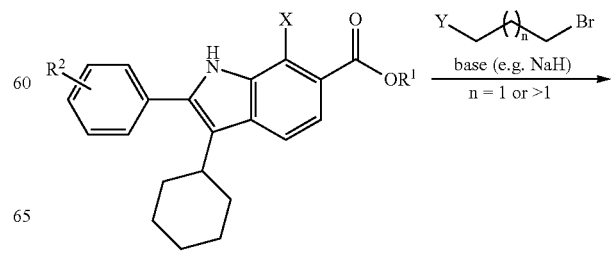

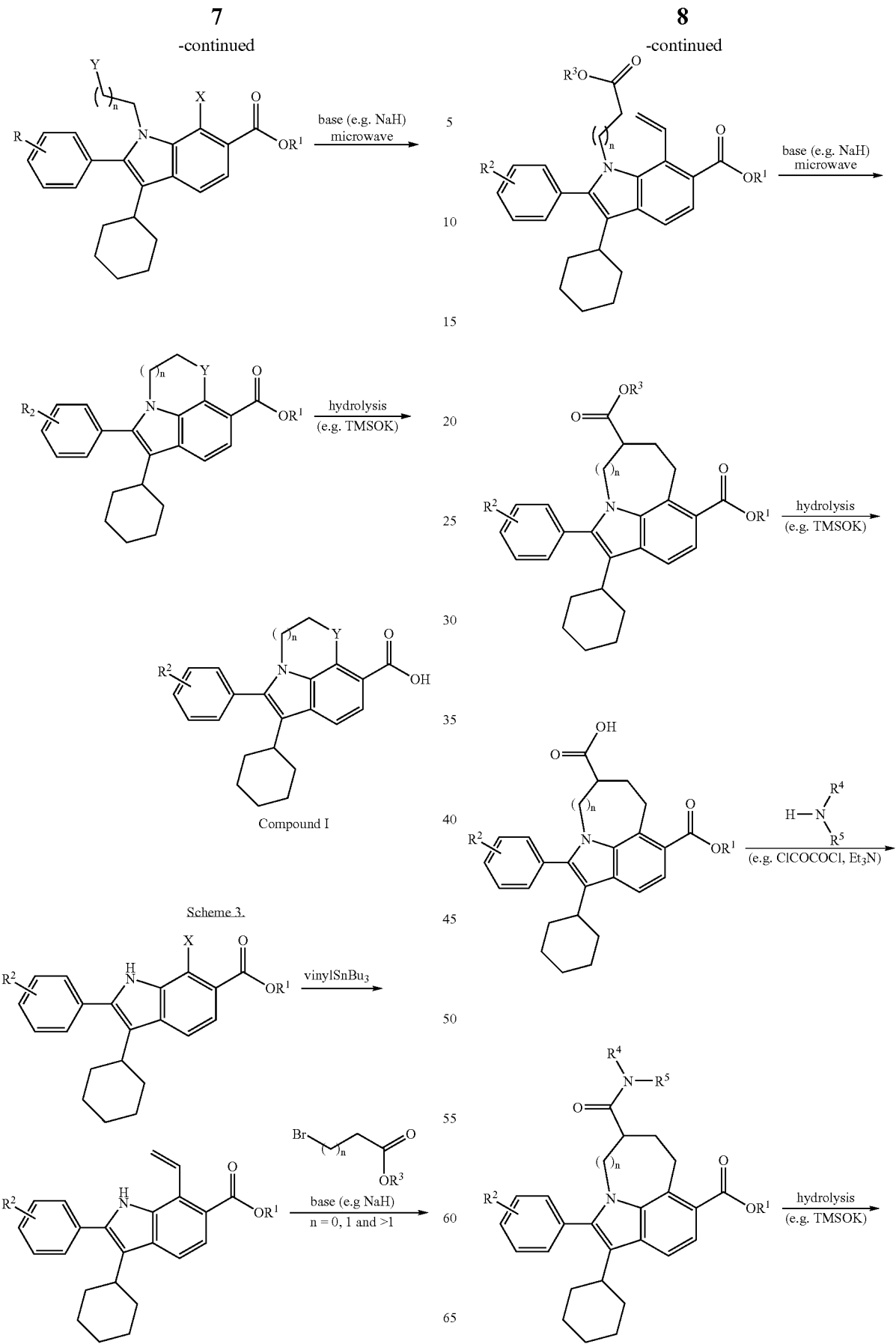

-continued

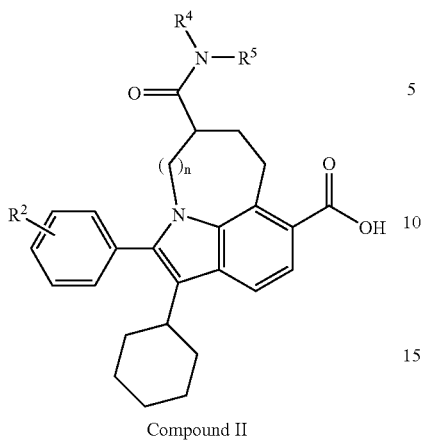

Compound II

Scheme 4.

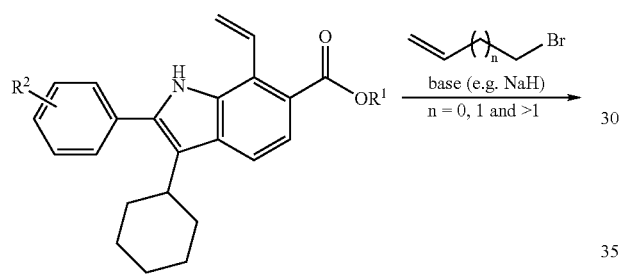

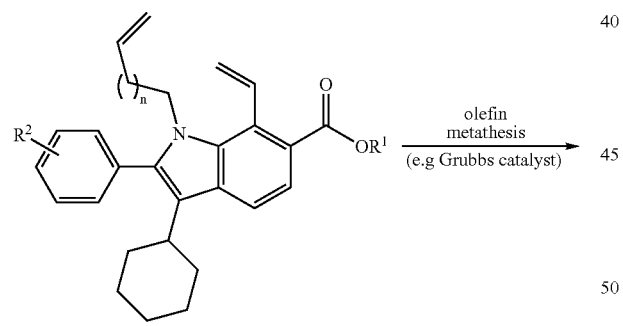

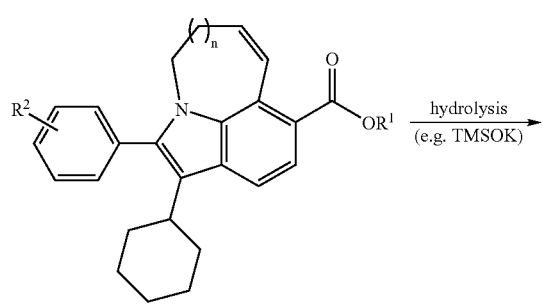

-continued

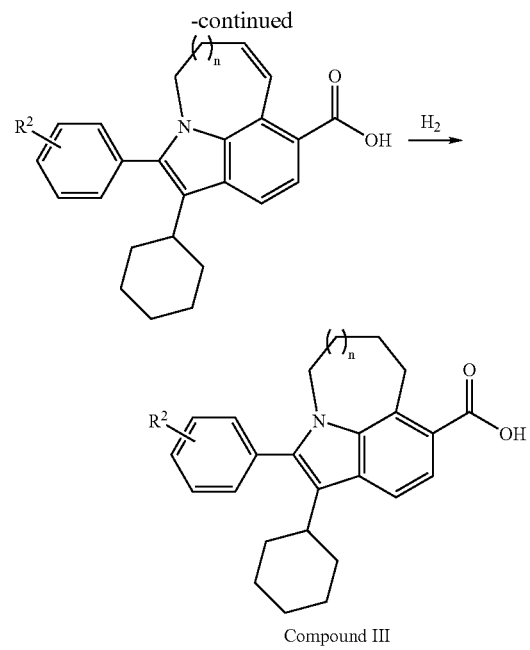

Compound III

Scheme 5.

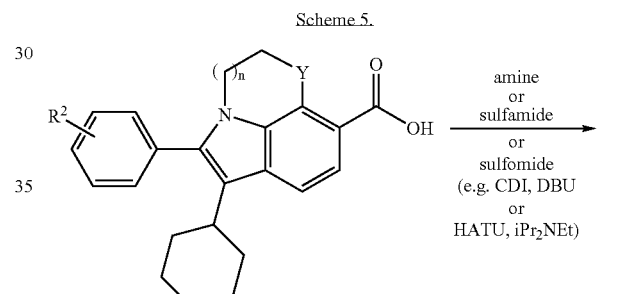

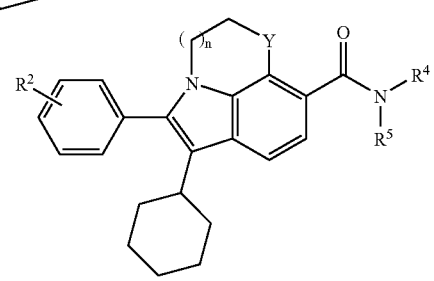

Biological Methods

Formula I compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

IC50 values for compounds were determined using seven different [I]. IC50 values were calculated from the inhibition using the formula $y = A + ((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH$_2$O, NaCl added to 150 mM final, the FRET peptide diluted to 20 uM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO$_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. EC$_{50}$ values for a protease inhibitor titration were calculated as the concentration which caused a 50% reduction in FRET or luciferase activity. The two numbers generated for the compound plate, percent cytotoxicity and percent activity were used to determine compounds of interest for further analysis.

Representative data for Formula I compounds are reported in Table 1.

TABLE 1

| Compound | IC$_{50}$ | EC$_{50}$ |
|---|---|---|
| (structure) | C | E |
| (structure) | A | A |
| (structure) | A | A |
| (structure) | C | E |
| (structure) | B | B |

TABLE 1-continued

| Compound | IC$_{50}$ | EC$_{50}$ |
|---|---|---|
| (structure: methyl ester, phenyl, cyclohexyl, methyl carboxylate on pyrrolizidine-fused system) | C | A |
| (structure: carboxylic acid, phenyl, cyclohexyl, methyl carboxylate) | A | E |
| (structure: morpholine amide, phenyl, cyclohexyl, methyl carboxylate) | A | E |
| (structure: morpholine amide, phenyl, cyclohexyl, dimethylsulfamoyl carboxamide) | D | D |

TABLE 1-continued
| Compound | IC$_{50}$ | EC$_{50}$ |
|---|---|---|
| 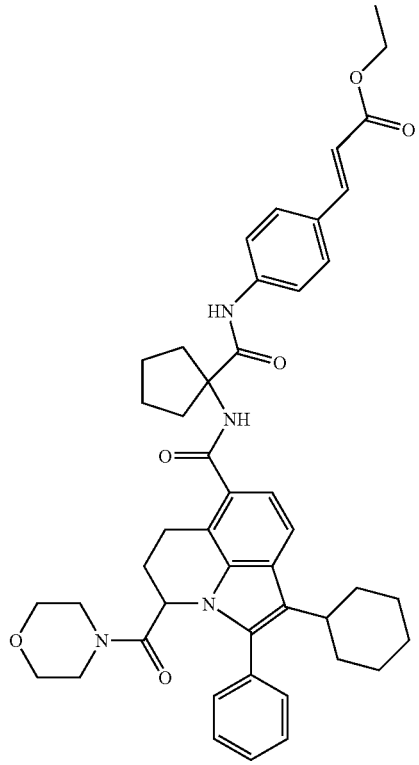 | D | B |
| 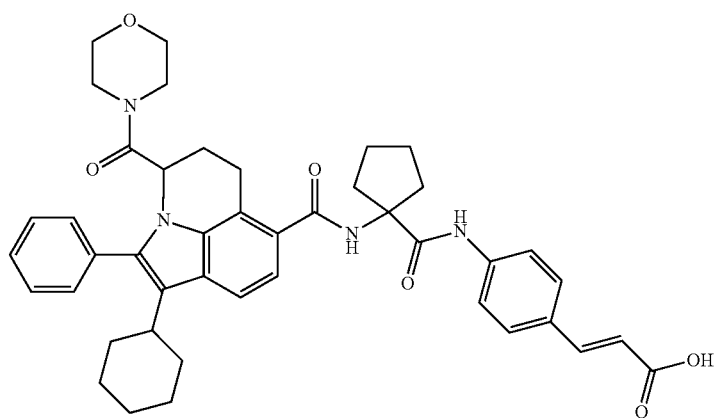 | B | D |
| 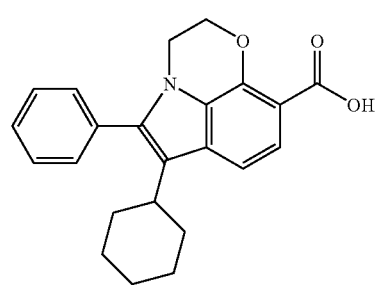 | B | D |

TABLE 1-continued

| Compound | IC$_{50}$ | EC$_{50}$ |
|---|---|---|
| (structure) | D | D |
| (structure) | B | A |
| (structure) | B | B |
| (structure) | D | C |

TABLE 1-continued
| Compound | IC$_{50}$ | EC$_{50}$ |
|---|---|---|
| 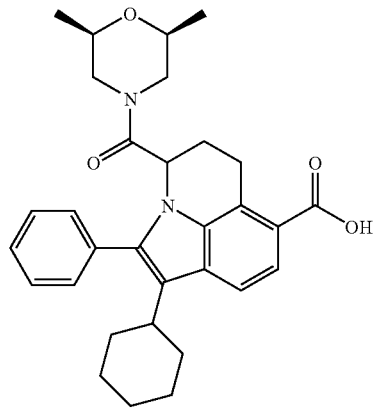 | A | D |
| 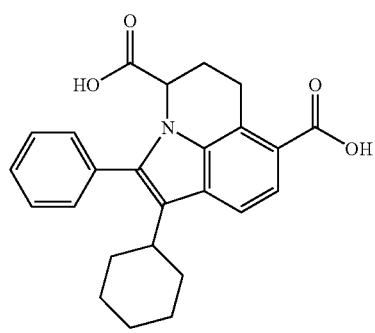 | A | C |
| 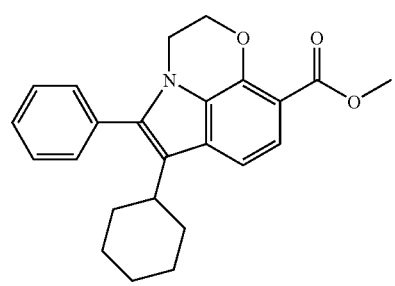 | D | E |

TABLE 1-continued
| Compound | IC$_{50}$ | EC$_{50}$ |
|---|---|---|
| 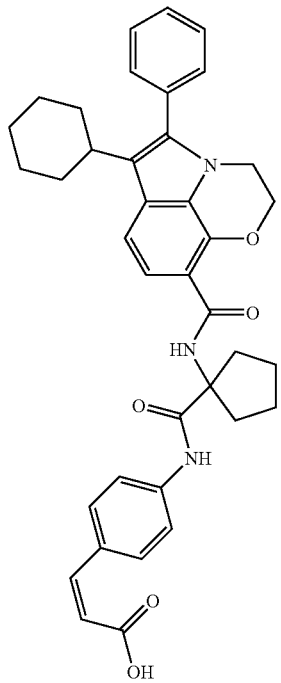 | B | B |
| 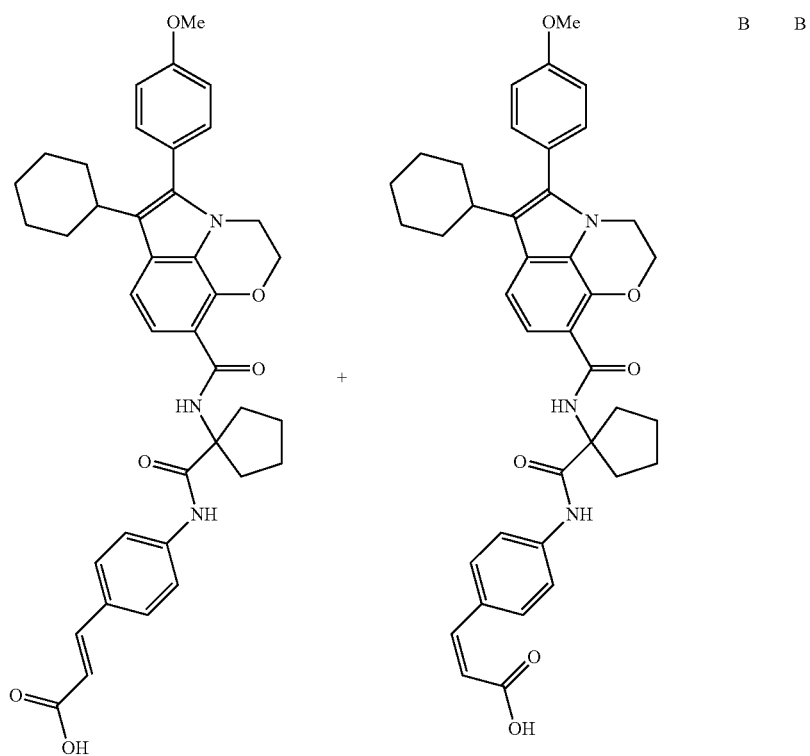 | B | B |

TABLE 1-continued

| Compound | IC$_{50}$ | EC$_{50}$ |
|---|---|---|
| (structure) | B | A |
| (structure) | A | A |
| (structure) | B | D |

A > 1 μM;
B 0.03 μM-1 μM;
C > 10 μM;
D 1 μM-10 μM;
E > 0.12 μM.
IC$_{50}$ values were determined using the preincubation protocol.
EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound or a pharmaceutically acceptable salt thereof. Another aspect of the invention is a method of inhibiting the function of the HCV replicon. Another aspect of the invention is a method of inhibiting the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |

TABLE 2-continued

| Brand Name | Type of Inhibitor or Target | Source Company |
|---|---|---|
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO 2005047288 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

Description of Specific Embodiments

Analytical HPLC and LC/MS were performed by using Shimadzu-VP instrument with UV detection at 220 nM and Waters Micromass. Biotage Horizon was used for flash chromatography as indicated. NMR spectra were collected by using Bucker DPX-300 MHz or DRX-500 MHz instruments.

Intermediate 1

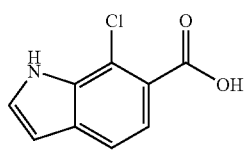

7-chloro-1H-indole-6-carboxylic acid. A two liter 3-neck flask was assembled with an overhead stir, flame dried and flushed with nitrogen. To this was added 1.0 equivalent of 2-chloro-3-nitrobenzoic acid (30 grams, 148.8 mmol) in 300 mL dry THF. The flask was then cooled to −45° C. with the aid of an ethanol/dry ice bath. 4.0 equivalents of cold Vinyl Grignard reagent (Aldrich, 1M Sure/Seal™ bottles) was then cannulated into the solution of nitrobenzoic acid. An additional 100 mL of dry THF was then added via cannula to the very thick solution. The flask was allowed to slowly warm to room temperature overnight. In the morning, the flask was cooled to 0° C. with an ice bath and 400 mL of saturated NH$_4$Cl was added in four portions. The mixture was stirred for one hour then transferred to a separatory funnel and extracted with ethyl acetate (300 mL×3). The organic layers were combined, washed with brine (100 mL), dried over MgSO$_4$ and evaporated to dryness on the rotovap. The aqueous layer was acidified to pH=2 with 2M HCl. The resulting solid was filtered, combined with the above isolated solid and dried in a vacuum desiccator over night to yield 26.32 grams (90%) of a tan powder that was used without further purification. $^1$H NMR (300 MHz): (CD$_3$OD) δ 7.59 (d, J=8.42 Hz, 1H), 7.49 (d, J=8.42 Hz, 1H), 7.42 (d, J=2.93 Hz, 1H), 6.53 (d, J=2.93 Hz, 1H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=195.92, 197.92, HPLC R$_t$=1.018 min.

Intermediate 2

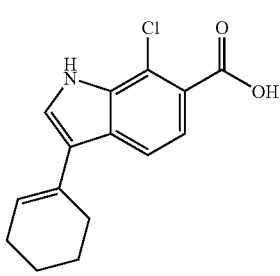

7-chloro-3-cyclohexenyl-1H-indole-6-carboxylic acid. To a one liter round bottom flask equipped with a reflux condenser was added 26.3 grams (0.135 mol) of 7-chloro-1H-indole-6-carboxylic acid and 200 mL of dry methanol. Three equivalents (41.8 mL, 0.404 mol) of cyclohexanone was added in one portion. The heterogeneous mixture was heated to 60° C. at which point all of the indole went into solution. 6.1 equivalents of a methanolic sodium methoxide solution (0.820 mol, 187 mL) was then added in two portions. The solution was heated at reflux overnight. In the morning, the reaction mixture was cooled and evaporated to dryness. The crude mixture was diluted with 75 mL of ethyl acetate and acidified with 1M HCl. The resulting solid was filtered, washed with cold ethyl acetate and dried overnight in a vacuum desiccator to yield 32.8 grams (88%) of a powder. $^1$H NMR (300 MHz, CD$_3$OD) δ 7.73 (d, J=8.42 Hz, 1H), 7.61 (d, J=8.42 Hz, 1H), 7.37 (s, 1H), 6.16 (br s, 1H), 2.42 (m, 2H), 2.24 (m, 2H), 1.79 (m, 2H), 1.68 (m, 2H), MS m/z 276.01 (M+H).

Intermediate 3

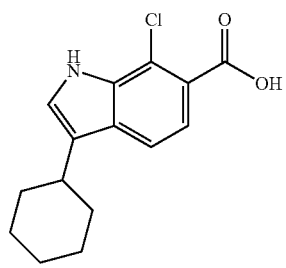

7-chloro-3-cyclohexyl-1H-indole-6-carboxylic acid. 32.6 grams (0.118 mol) of 7-chloro-3-cyclohexenyl-1H-indole-6-carboxylic acid was added to a one liter round bottom flask along with 250 mL of a 1:1 (v/v) mixture of THF and methanol. 3.3 grams of 20% palladium hydroxide on carbon was then added and the flask was fitted with a septa and balloon of hydrogen. The mixture was stirred overnight at room temperature. In the morning, the crude product was filtered through a pad of celite and the pad was washed with THF. The product was evaporated to dryness and triturated with cold diethyl ether to give 32.1 grams of a tan solid (98% yield, 85% purity, UV detection λ=220 nm) that was used without further purification. MS m/z 278.00 (M+H).

Intermediate 4

Methyl 7-chloro-3-cyclohexyl-1H-indole-6-carboxylate. To 27.2 grams (97.9 mmol) of 7-chloro-3-cyclohexyl-1H-indole-6-carboxylic acid in 200 mL of dry methanol in a 500 mL round bottom flask was added 0.05 equivalents (4.9 mmol, 357 μl) of thionyl chloride. The solution was refluxed for 36 hours at which point an additional 0.05 equivalents of thionyl chloride was added. The solution was refluxed for an additional 24 hours. The crude product was cooled to room temperature and evacuated to near dryness. The product was diluted with ethyl acetate and hexane and purified by flash chromatography (5:1 Hexane/Ethyl acetate) to give 21.5 grams of a yellow crystalline solid (75%). $^1$H NMR (500 MHz, CDCl$_3$) 8.42 (br s, 1H), 7.68 (d, J=8.24 Hz, 1H), 7.55 (d, J=8.24 Hz, 1H), 7.13 (d, J=2.45 Hz, 1H), 3.94 (s, 3H), 2.79 (m, 1H), 2.05 (m, 2H), 1.84 (m, 2H), 1.80 (m, 1H), 1.45 (m, 4H), 1.30 (m, 1H). MS m/z 292.12 (M+H).

Alternatively, methyl 7-chloro-3-cyclohexyl-1H-indole-6-carboxylate was prepared as follows:

Methyl 7-chloro-3-cyclohexyl-1H-indole-6-carboxylate. To a mixture of 7-chloro-1H-indole-6-carboxylic acid (3.8 g, about 19.4 mmol) in MeOH (50 ml) at r.t. under N$_2$ was added cyclohexanone (6.13 ml, 59.1 mmol), followed by a solution of NaOMe in MeOH (17.5 ml, 76.6 mmol, 25% wt). The reaction mixture was stirred at reflux for 16 hr. After cooling to r.t., the mixture was added another bath of cyclohexanone (6.13 ml, 59.1 mmol), followed by another solution of NaOMe in MeOH (17.5 ml, 76.5 mmol, 25% wt), and then re-stirred at reflux for another 7 hr. After cooling to r.t., the mixture was evaporated, added with water (100 ml), acidified with hydrochloric acid (5N) and left standing at r.t. overnight. The aqueous mixture was decanted, and the residue washed twice with hydrochloric acid (30 ml, 1N) and twice with water (30 ml). The residue was further washed three times with hexane, and then dried to give 5.5 g of 7-chloro-3-cyclohexenyl-1H-indole-6-carboxylic acid. Another 2.6 g of the product was obtained from another reaction using 2.27 g of 7-chloro-1H-indole-6-carboxylic acid. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=275.94, 277.94, HPLC R$_t$=1.750 min. To a mixture of the 7-chloro-3-cyclohexenyl-1H-indole-6-carboxylic acid (8.1 g) obtained from above in a mixture of THF/MeOH (25 ml/25 ml) at r.t. under N$_2$ was added Pd(OH)$_2$/C (764 mg, 20%). The mixture was then flushed with a stream of hydrogen gas using a balloon, and then stirred under hydrogen (using a balloon) for 27 hr. After removing the hydrogen balloon, the mixture was then flushed with a stream of N$_2$, and then filtered through a cake of celite. The filtrate was evaporated to give 7-chloro-3-cyclohexyl-1H-indole-6-carboxylic acid (7.7 g). Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=278.01, 280.00, HPLC R$_t$=1.773 min.

To a mixture of 7-chloro-3-cyclohexyl-1H-indole-6-carboxylic acid obtained from above in a mixture of PhH/MeOH (40 ml/40 ml) at 0° C. (ice-water bath) under N$_2$ was added dropwise a solution of TMSCHN$_2$ in hexane (31 ml, 62 mmol, 2M). After removing the cooling bath, the reaction mixture was left stirring at r.t. for 2 hr 15 min. The reaction was then quenched by adding excess AcOH (about 5 ml) dropwise over about 15 min until no further gas evolution was observed. After evaporation, the residue was purified by Biotage flash chromatography (gradient elution, 0 to 20% EtOAc/Hexane) to gave the product methyl ester (methyl 7-chloro-3-cyclohexyl-1H-indole-6-carboxylate) (2.5 g over the 3 steps). $^1$H NMR (500 MHz): (CD$_3$OD) δ 7.59 (d, J=8.5, 1H), 7.57 (d, J=8.5, 1H), 7.25 (s, 1H), 3.93 (s, 3H), 2.83 (b m, 1H), 2.08-2.07 (b d, 2H), 1.89-1.87 (b m, 2H), 1.81-1.79 (b d, 1H), 1.54-1.49 (m, 4H), 1.40-1.30 (b m, 1H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=292.13, 294.12, HPLC R$_t$=1.958 min.

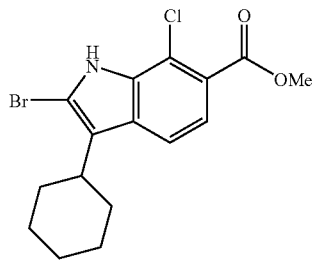

Intermediate 5

Methyl 2-bromo-7-chloro-3-cyclohexyl-1H-indole-6-carboxylate. To a mixture of the methyl 7-chloro-3-cyclohexyl-1H-indole-6-carboxylate (1 g, 3.43 mmol) in a mixture of THF/CH$_2$Cl$_2$ (9 ml/9 ml) at r.t. under N$_2$ was added pyridinium tribromide (1.33 g, 4.16 mmol, recrystallized from AcOH), and the reaction mixture stirred at r.t. for 2 hr. The mixture was then diluted with CH$_2$Cl$_2$ (40 ml), and the organics washed with NaHCO$_3$ (30 ml, sat. aq.), followed by hydrochloric acid (30 ml, 1N) and brine (30 ml). After concentration of the organic layer, the residue was purified by Biotage flash chromatography (gradient elution, 0 to 20% EtOAc/Hexane) to gave methyl 2-bromo-7-chloro-3-cyclohexyl-1H-indole-6-carboxylate (841.8 mg, 66%) and to recover the starting material (201 mg). $^1$H NMR (500 MHz): (CD$_3$OD) δ 7.67 (b d, J=8.5, 1H), 7.59 (d, J=8.5, 1H), 3.93 (s, 3H), 2.89 (m, 1H), 2.00-1.90 (overlapping m, 4H), 1.83-1.78 (overlapping m, 3H), 1.50-1.40 (m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=370.02, 372.03, 374.02, HPLC R$_t$=2.002 min.

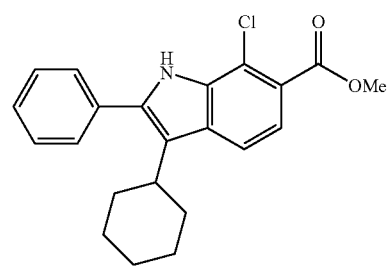

Intermediate 6

7-chloro-3-cyclohexyl-2-phenyl-1H-indole-6-carboxylic acid, methyl ester. To a mixture of methyl 2-bromo-7-chloro-3-cyclohexyl-1H-indole-6-carboxylate (841.8 mg, 2.27 mmol), phenylboronic acid (409 mg, 3.35 mmol), Pd(PPh$_3$)$_4$ (267 mg, 0.231 mmol), LiCl (188 mg, 4.44 mmol) and Na$_2$CO$_3$ (589 mg, 5.56 mmol) under N$_2$ at r.t. in a re-usuable sealed tube was charged with a mixture of PhMe/EtOH (10 ml/10 ml) and then water (6.6 ml). The sealed tube was closed and the reaction mixture stirred at 60° C. for 3 hr, left standing at r.t. overnight, and then re-stirred at 60° C. for 2 hr 40 min. After cooling to r.t., the mixture was partitioned between CH$_2$Cl$_2$ and H$_2$O (50 ml/50 ml). The organic layer was separated and evaporated to give a residue, which was purified by Biotage flash chromatography (gradient elution, 0 to 20% EtOAc/Hexane) to gave 1H-indole-6-carboxylic acid, 7-chloro-3-cyclohexyl-2-phenyl-, methyl ester (755 mg, 90%). $^1$H NMR (500 MHz): (CD$_3$OD) δ 7.77 (d, J=8.3, 1H), 7.61 (d, J=8.3, 1H), 7.58-7.52 (overlapping m, 4H), 7.47 (m, 1H), 3.95 (s, 3H), 2.92 (m, 1H), 2.03 (m, 2H), 1.88-1.78 (overlapping m, 5H), 1.38 (m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$= 368.06, 370.03, HPLC R$_t$=2.085 min.

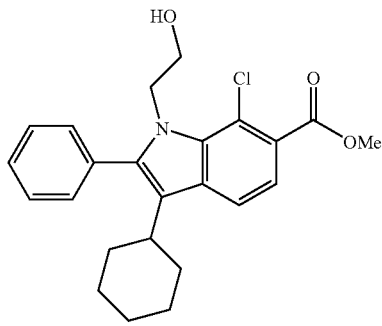

Intermediate 8

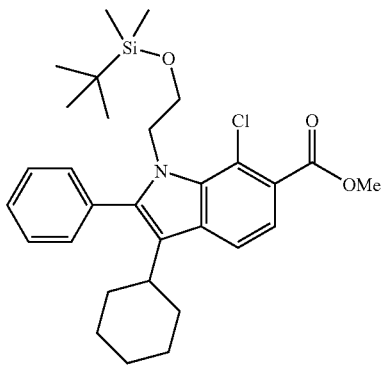

Intermediate 7

7-chloro-3-cyclohexyl-1-[2-[[(1,1-dimethylethyl)dimethylsilyl]oxy]ethyl]-2-phenyl-1H-indole-6-carboxylic acid, methyl ester. To a mixture of the chloro-indole (1H-indole-6-carboxylic acid, 7-chloro-3-cyclohexyl-2-phenyl-, methyl ester) (504.2 mg, 1.37 mmol) in DMSO (5 ml) under N$_2$ at r.t. was added NaH (110 mg, 2.75 mmol, 60% oil), and the reaction mixture stirred for about 10 min. The (2-bromoethoxy)-tert-butyldimethylsilane (0.44 ml, 2.05 mmol) was then added, followed by KI (340 mg, 2.05 mmol), and the reaction mixture stirred at r.t. for 19 hr. The mixture was acidified with hydrochloric acid (1N), diluted with water and the then extracted with CH$_2$Cl$_2$ (30 ml). The organic extract was evaporated, and the residue purified by Biotage flash chromatography (gradient elution, 0 to 20% EtOAc/Hexane) to gave the tert-butyldimethylsilyl ether (1H-indole-6-carboxylic acid, 7-chloro-3-cyclohexyl-1-[2-[[(1,1-dimethylethyl)dimethylsilyl]oxy]ethyl]-2-phenyl-, methyl ester) as a colorless oil (572.3 mg, 79%). $^1$H NMR (300 MHz): (CD$_3$OD) δ 7.74 (d, J=8.3, 1H), 7.54-7.52 (b m, 3H), 7.48 (d, J=8.3, 1H), 7.44-7.41 (b m, 2H), 4.50 (t, J=6, 2H), 3.94 (s, 3H), 3.71 (t, J=6, 2H), 2.55-2.70 (m, 1H), 1.90-1.65 (b m, 7H), 1.35-1.15 (b m, 3H) 0.70 (s, 9H), −0.22 (s, 6H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=526.32, 528.32, HPLC R$_t$=2.577 min.

7-chloro-3-cyclohexyl-1-(2-hydroxyethyl)-2-phenyl-1H-indole-6-carboxylic acid, methyl ester. To a mixture of the tert-butyldimethylsilyl ether (1H-indole-6-carboxylic acid, 7-chloro-3-cyclohexyl-1-[2-[[(1,1-dimethylethyl)dimethylsilyl]oxy]ethyl]-2-phenyl-, methyl ester) (38.3 mg, 72.8 µmol) in THF (1 ml) at r.t. under N$_2$ was added a solution of tetrabutylammonium fluoride (TBAF) in THF (0.15 ml, 150 µmol, 1M). The reaction mixture was stirred at r.t. for 2 hr. After evaporation, the residue was washed with water (3×2 ml), and then hexane (3×2 ml) and dried. Purification by Biotage flash chromatography (gradient elution, 10 to 50% EtOAc/Hexane) gave the primary alcohol (1H-indole-6-carboxylic acid, 7-chloro-3-cyclohexyl-1-(2-hydroxyethyl)-2-phenyl-, methyl ester) (27.4 mg, 91%). $^1$H NMR (300 MHz): (CD$_3$OD) δ 7.75 (d, J=8.4, 1H), 7.58-7.54 (b m, 3H), 7.47 (d, J=8.4, 1H), 7.43-7.41 (b m, 2H), 4.47 (t, J=6.9, 2H), 3.95 (s, 3H), 3.65 (t, J=6.9, 2H), 2.67-2.50 (m, 1H), 1.90-1.65 (b m, 7H), 1.35-1.15 (b m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=412.12, 414.11, HPLC R$_t$=2.018 min.

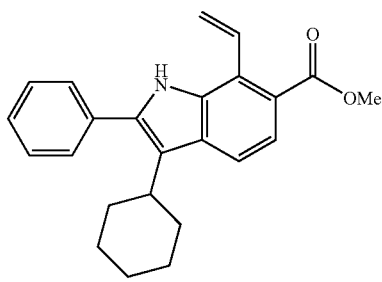

Intermediate 9

3-cyclohexyl-7-ethenyl-2-phenyl-1H-indole-6-carboxylic acid, methyl ester. To a mixture of 1H-indole-6-carboxylic acid, 7-chloro-3-cyclohexyl-2-phenyl-, methyl ester (678.1 mg, 1.84 mmol), CsF (1.13 g, 7.44 mmol) and (tBu$_3$P)$_2$Pd (197 mg, 0.39 mol) under N$_2$ in a reusable sealed tube was added 1,4-dioxane (25 ml) and then tributylvinyltin (5.5 ml, 18.8 mmol). The reaction mixture was stirred at 120° C. for 2 hr, and then left at r.t. overnight. After stirring at 120° C. for another 6 hr, the mixture was added another batch of (tBu$_3$P)$_2$Pd (197 mg, 0.39 mmol) and tributylvinyltin (5.5 ml, 18.8 mmol), and stirred at 120° C. again for another 2 hr. The volatile was then evaporated and the residue purified by Biotage flash chromatography (gradient elution, 0 to 20% EtOAc/Hexane) to gave the product 1H-indole-6-carboxylic acid, 3-cyclohexyl-7-ethenyl-2-phenyl-, methyl ester as a yellow solid (646.8 mg, 98%). $^1$H NMR (300 MHz): (CD$_3$OD) δ 7.74 (d, J=8.6, 1H), 7.62 (d, J=8.6, 1H), 7.53-7.43 (b m, 5H), 7.38 (dd, J=17.7, 11.4, 1H), 5.64 (d, J=17.7, 1H), 5.61 (d, J=11.4, 1H), 3.89 (s, 3H), 2.93 (m, 1H), 2.15-1.95 (b m, 2H), 1.90-1.75 (b m, 5H), 1.50-1.25 (b m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=360.16, HPLC R$_f$=2.097 min.

Intermediate 10

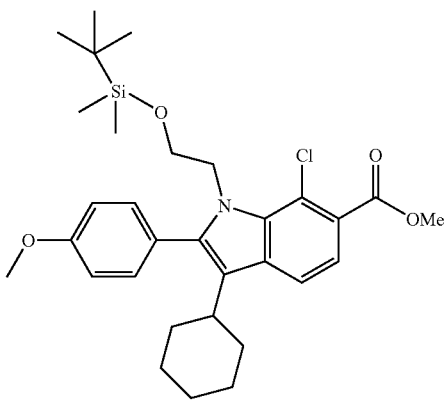

Methyl-1-(2-(tert-butyldimethylsilyloxy)ethyl)-7-chloro-3-cyclohexyl-2-(4-methoxyphenyl)-1H-indole-6-carboxylate. To a mixture of Methyl-7-chloro-3-cyclohexyl-2-(4-methoxyphenyl)-1H-indole-6-carboxylate (115.7 mgs, 291 μmol) in 2 mL of DMSO under N$_2$ was added NaH (95%, 2 equivalents, 582 μmol, 14.0 mgs), and the reaction mixture was stirred for 20 minutes. (2-bromoethoxy)-tert-butyldimethylsilane (1.5 equivalents, 436 μmol, 94 μL) was then along with KI (1.5 equivalents, 72.4 mgs), and the reaction was stirred at room temperature overnight. The crude product was acidified with 1 M HCl, diluted with water and extracted with dichloromethane. The extracted product was concentrated en vacuo then purified by automated flash chromatography (Biotage Horizon™, gradient elution, 5 to 40% Ethyl Acetate/Hexane) to give 136.0 mgs (86%) of Methyl-1-(2-(tert-butyldimethylsilyloxy)ethyl)-7-chloro-3-cyclohexyl-2-(4-methoxy phenyl)-1H-indole-6-carboxylate as a oily colorless solid. The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 2 minute hold at a rate of 5 mL/minute. The NMR spectra was recorded at room temperature using a Bruker DRX300 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). 1H NMR (300 MHz, CDCl$_3$) δ 7.90 (d, J=8.05 Hz, 1H), 7.73 (d, J=8.05 Hz, 1H), 7.50 (d, J=8.42 Hz, 2H), 7.24 (d, J=8.42 Hz, 2H), 4.69 (t, J=6.40 Hz, 2H), 4.17 (s, 3H), 4.12 (s, 3H), 3.95 (t, J=6.40 Hz, 2H), 2.79 (m, 1H), 1.96 (m, 6H), 1.41-1.56 (m, 3H), 1.11-1.20 (m, 1H), 0.95 (s, 9H), 0.03 (s, 6H). MS m/z 557.23 (M+H), Rf 3.05 min., 100% purity.

Intermediate 11

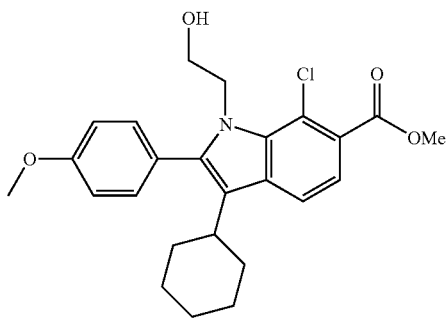

Methyl-7-chloro-3-cyclohexyl-1-(2-hydroxyethyl)-2-(4-methoxyphenyl)-1H-indole-6-carboxylate. To a mixture of 131 mgs (1 equivalents, 236 μmol) of Methyl-1-(2-(tert-butyldimethyl silyloxy)ethyl)-7-chloro-3-cyclohexyl-2-(4-methoxy phenyl)-1H-indole-6-carboxylate in 4 mL of THF was added under N$_2$ a 1 M solution of tetrabutylammonium fluoride in THF (2 equivalents, 471 μL). The reaction mixture was stirred for two hours at room temperature. The solution was concentrated en vacuo, washed with water and the product extracted with ethyl acetate. Automated flash chromatography (Biotage Horizon™, gradient elution, 10 to 50% Ethyl Acetate/Hexane) gave 97.0 mgs (93%) of Methyl-7-chloro-3-cyclohexyl-1-(2-hydroxyethyl)-2-(4-methoxyphenyl)-1H-indole-6-carboxylate. The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute. The NMR spectra was recorded at room temperature using a Bruker DRX300 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). 1H NMR (300 MHz, CDCl$_3$) δ 7.67 (d, J=8.42 Hz, 1H), 7.50 (d, J=8.42 Hz, 1H), 7.25 (d, J=8.78 Hz, 2H), 7.01 (d, J=8.78 Hz, 2H), 4.50 (t, J=6.22 Hz, 2H) 3.94 (s, 3H), 3.89 (s, 3H), 3.76 (t, J=6.22 Hz, 2H), 2.55 (m, 1H), 1.71 (m, 6H) 1.38 (m, 1H) 1.23 (m, 3H). MS m/z 442.15 (M+H), Rf 2.20 min., 96.4% purity.

Intermediate 12

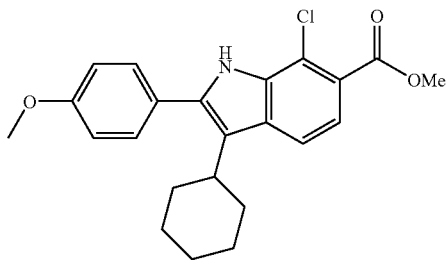

Methyl-7-chloro-3-cyclohexyl-2-(4-methoxyphenyl)-1H-indole-6-carboxylate. To 572.0 mgs (1.54 mmol) of Methyl-2-bromo-7-chloro-3-cyclohexyl-1H-indole-6-carboxylate in 8 mL of toluene and 8 mL of ethanol was added 2 equivalents of LiCl (3.08 mmol, 130.6 mgs), 2.5 equivalents of Na$_2$CO$_3$ (3.85 mmol, 408.1 mgs) in 4 mL of water, and 1.5 equivalents of para-methoxyphenyl boronic acid (2.31 mmol, 351.0 mgs). To this mixture was then added 0.1 equivalents of PdCl$_2$(PPh$_3$)$_2$ (150.0 μmol, 105.3 mgs), and the mixture was degassed then flushed with N$_2$ (×3). The reaction mixture was heated to 70° C. overnight. After 18 hours, the mixture was cooled to room temperature, concentrated to near dryness then extracted with ethyl acetate. The crude product was purified using automated flash chromatography (Biotage Horizon™, gradient elution, 0 to 40% Ethyl Acetate/Hexane) to give 502.0 mgs (82%) of Methyl-7-chloro-3-cyclohexyl-2-(4-methoxyphenyl)-1H-indole-6-carboxylate as an ivory colored solid. The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute.

The NMR spectra was recorded at room temperature using a Bruker DRX 500 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). $^1$H NMR (500 MHz, CDCl$_3$) δ 8.32 (br s, 1H), 7.69 (m, 2H), 7.44 (d, J=8.54 Hz, 2H), 7.03 (d, J=8.54 Hz, 2H), 3.94 (s, 3H), 3.88 (s, 3H), 2.88 (m, 1H), 1.94 (m, 2H), 1.84 (m, 4H), 1.56 (m, 1H), 1.34 (m, 3H). MS m/z 398.14 (M+H), Rf 2.30 min., 92.0% purity.

EXAMPLE 1

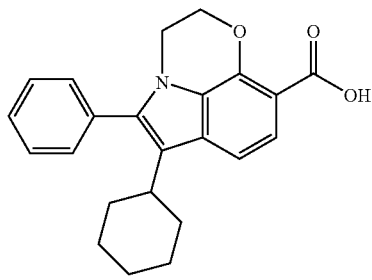

6-cyclohexyl-2,3-dihydro-5-phenyl-1,4-oxazino[2,3,4-hi]indole-9-carboxylic acid. To a mixture of the alcohol (1H-indole-6-carboxylic acid, 7-chloro-3-cyclohexyl-1-(2-hydroxyethyl)-2-phenyl-, methyl ester) (27.4 mg, 66.5 μM) in DMSO (1.0 ml) under N$_2$ at r.t. in a microwave reaction tube was added NaH (5.3 mg, 133 μmol, 60% in oil), and the reaction mixture stirred for about 10 min. The reaction mixture was then placed under microwave irradiation in an Emrys Optimizer (*Personal Chemistry*) at 200° C. and with the absorption level set to high for 10 min. The mixture was then diluted with water (1 ml) and acidified with hydrochloric acid (1N). The solid was filtered, washed with water (1 ml) and dried. Purification by preparative thin layer chromatography (500 μm×20 cm×20 cm plate) using 5% MeOH/CH$_2$Cl$_2$ as eluent gave (1,4-oxazino[2,3,4-hi]indole-9-carboxylic acid, 6-cyclohexyl-2,3-dihydro-5-phenyl-) as an off white solid. $^1$H NMR (300 MHz): (CD$_3$OD) δ 7.59-7.44 (d overlapping with m, 6H), 7.35 (d, J=8.7, 1H), 4.59 (t, J=4.8, 2H), 4.12 (t, J=4.8, 2H), 2.79-2.70 (m, 1H), 2.04-1.91 (b m, 2H), 1.86-1.74 (b m, 4H), 1.37-1.31 (b m, 4H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$= 362.23, HPLC R$_f$=1.952 min.

EXAMPLE 2

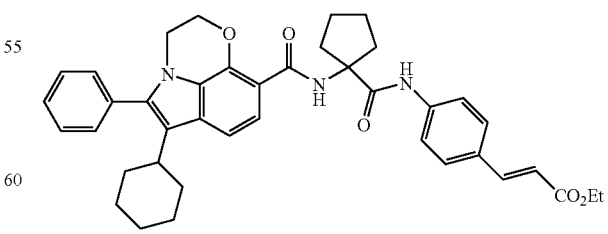

6-cyclohexyl-N-[(dimethylamino)sulfonyl]-2,3-dihydro-5-phenyl-1,4-oxazino[2,3,4-hi]indole-9-carboxamide. To the acid (1,4-oxazino[2,3,4-hi]indole-9-carboxylic acid, 6-cyclohexyl-2,3-dihydro-5-phenyl-) (11.4 mg, 31.5 μmol) in a round-bottomed flask at r.t. under N$_2$ was added a solution of 1,1'-carbonyldiimidazole (CDI) (10.2 mg, 62.9 μmol) in THF (1 ml), and the mixture was stirred at 50° C. for 2 hr. After cooling to r.t., the reaction mixture was added a mixture of N,N-dimethylsulfamide (15.6 mg, 126 μmol) and DBU (21.6 mg, 142 μmol) in THF (0.5 ml), and then stirred at 50° C. for 20.5 hr. After cooling to r.t., the volatiles were evaporated and the residue added hydrochloric acid (1.5 ml, 1N). The aqueous mixture was removed by pipet, and the solid residue purified by preparative thin layer chromatography (250 μm×20 cm×20 cm plate) using 5% MeOH/CH$_2$Cl$_2$ as eluent to give the product, which was then further purified by preparative thin layer chromatography (250 μm×20 cm×20 cm plate) using 20% EtOAc/Hexane as eluent to give the sulfamide (1,4-oxazino[2,3,4-hi]indole-9-carboxamide, 6-cyclohexyl-N-[(dimethylamino)sulfonyl]-2,3-dihydro-5-phenyl-). $^1$H NMR (500 MHz): (CDCl$_3$—CD$_3$OD) δ 7.60-7.44 (d overlapping with m, 7H), 4.76 (t, J=4.8, 2H), 4.19 (t, J=4.8, 2H), 3.03 (s, 6H), 2.80-2.70 (m, 1H), 2.05-1.88 (b m, 2H), 1.88-1.70 (b m, 4H), 1.45-1.25 (b m, 4H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=468.14, HPLC R$_f$=1.987 min.

EXAMPLE 3

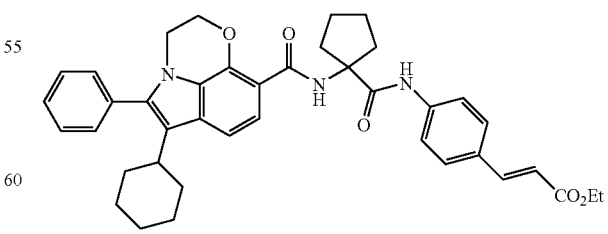

(2E)-3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-2-propenoic acid, ethyl ester. To a mixture of the acid 1,4-oxazino[2,3,4-hi]indole-9-carboxylic acid, 6-cyclohexyl-2,3-dihydro-5-phenyl- (23.5 mg, 65 μmol) in DMF (1 ml) at r.t. under N₂ was added the amine (40 mg, 132 μmol), 2-(1H-benzotriazole-1-yl)-1,1,3,3-tetramethyluronium tetrafluoroborate (TBTU) (65 mg, 197 μmol) and then N,N-diisopropylethylamine (45 μl, 258 μmol), and the reaction mixture stirred at r.t. for 20 hr. The volatile was evaporated and the residue added hydrochloric acid (2 ml, 1N). After removing the aqueous mixture was removed by pipet, the residue was washed with water (2 ml). The aqueous mixture was again removed by pipet. The residue was dried, and purified by Biotage flash chromatography (gradient elution, 0 to 50% EtOAc/Hexane) gave the amide (2-propenoic acid, 3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-, ethyl ester, (2E)-) (26.8 mg). ¹H NMR (500 MHz): (CD₃OD) δ 7.65-7.62 (m overlapping with two d, 1H), 7.64 (d overlapping with d, J=16, 1H), 7.64 (d, J=8.5, 1H), 7.58-7.49 (overlapping with m, 6H), 7.46 (d, J=7, 2H), 7.39 (d, J=8.5, 1H), 6.44 (d, J=16, 1H), 4.74 (m, 2H), 4.25 (q, J=7, 2H), 4.18 (m, 2H), 2.78-2.73 (m, 1H), 2.50-2.44 (b m, 2H), 2.18-2.14 (b m, 2H), 1.99-1.78 (b m, 10H), 1.42-1.25 (m overlapping with t, 4H), 1.33 (t, J=7, 3H); Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=646.26, HPLC R$_t$=2.160 min.

EXAMPLE 4

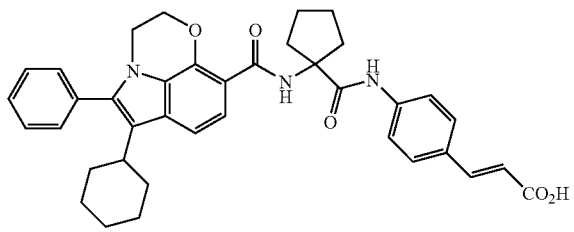

(2E)-3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-2-propenoic acid. To the ethyl ester (2-propenoic acid, 3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-, ethyl ester, (2E)-) (25.2 mg, 39 μmol) in a round-bottomed flask at r.t. under N₂ was added a THF solution (1 ml) of potassium trimethylsilanoate (TMSOK) (6 mg, about 42.1 μmol, 90% tech.), and the reaction mixture stirred for 75 min. Another batch of TMSOK (30 mg) was then added to the mixture. After stirring at r.t. for 2 hr, a further batch of TMSOK (30 mg) was added to the reaction mixture, which was then stirred for 16 hr. The mixture was acidified with hydrochloric acid (1N), and then concentrated. The residue was purified by preparative thin layer chromatography (250 μm×20 cm×20 cm plate) using 10% MeOH/CH₂Cl₂ as eluent to give the product, which was then further purified by another preparative thin layer chromatography (250 μm×20 cm×20 cm plate) using 5% MeOH/CH₂Cl₂ as eluent to give the acid (2-propenoic acid, 3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-, (2E)-). ¹H NMR (500 MHz): (CD₃OD) δ 7.65-7.62 (m overlapping with two d, 1H), 7.64 (d overlapping with d, J=16, 1H), 7.63 (d, J=8.5, 1H), 7.59-7.50 (overlapping with m, 6H), 7.47 (d, J=7, 2H), 7.41 (d, J=9, 1H), 6.41 (d, J=16, 1H), 4.75 (m, 2H), 4.19 (m, 2H), 2.78-2.73 (m, 1H), 2.50-2.45 (b m, 2H), 2.18-2.16 (b m, 2H), 2.00-1.74 (b m, 10H), 1.39-1.25 (b m, 4H); Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=618.26, HPLC R$_t$=2.018 min.

EXAMPLE 5

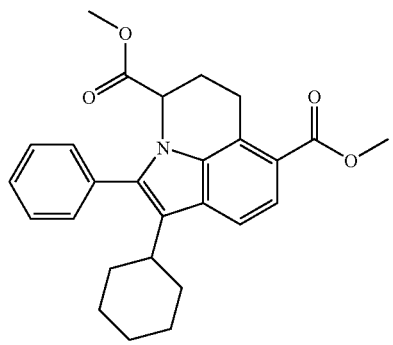

1-cyclohexyl-5,6-dihydro-2-phenyl-4H-pyrrolo[3,2,1-ij]quinoline-4,7-dicarboxylic acid, dimethyl ester. To a mixture of the vinylindole (1H-indole-6-carboxylic acid, 3-cyclohexyl-7-ethenyl-2-phenyl-, methyl ester) (357.9 mg, 0.966 mmol) in DMSO (6 ml) under N₂ at r.t. in a microwave reaction tube was added NaH (82.1 mg, 2.05 mmol, 60% in oil), and the reaction mixture stirred for about 10 min. The reaction mixture was added a DMSO solution (1 ml) of tert-butyl 2-bromoacetate (292.2 mg, 1.50 mmol), and stirred at r.t. for 2 hr. Another batch of NaH (82.1 mg, 2.05 mmol, 60% in oil) was added to the reaction mixture, which was then stirred for 10 min. The reaction mixture was then placed under microwave irradiation in an Emrys Optimizer (Personal Chemistry) at 200° C. and with the absorption level set to high for 10 min. The mixture was acidified with hydrochloric acid (1N), diluted with water, and the brown precipitates were filtered and dried. The material was then dissolved in a mixture of benzene/MeOH (10 ml/10 ml), and added with TMSCHN₂ (4.3 ml, 8.6 mmol, 2M in hexane). The reaction was then stirred at r.t. for 1 hr 40 min., quenched with AcOH and the volatiles were evaporated. The residue was purified by Biotage flash chromatography (gradient elution, 0 to 20% EtOAc/Hexane) to gave the dimethyl ester (4H-pyrrolo[3,2,1-ij]quinoline-4,7-dicarboxylic acid, 1-cyclohexyl-5,6-dihydro-2-phenyl-, dimethyl ester) (246.2 mg, 57%). ¹H NMR (300 MHz): (CD₃OD) δ 7.71 (d, J=8.6, 1H), 7.64 (d, J=8.6, 1H), 7.51-7.50 (m, 3H), 7.34-7.32 (b m, 2H), 4.84 (m, overlapping with CD₃OD peak, 1H), 3.90 (s, 3H), 3.73-3.66 (b m, 1H), 3.61 (s, 3H), 2.93 (m, 1H), 2.65-2.56 (b overlapping m, 2H), 2.29 (m, 1H), 1.96-1.72 (b overlapping m, 7H), 1.40-1.20 (b m, 3H); Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=432.26, HPLC R$_t$=2.090 min.

EXAMPLE 6

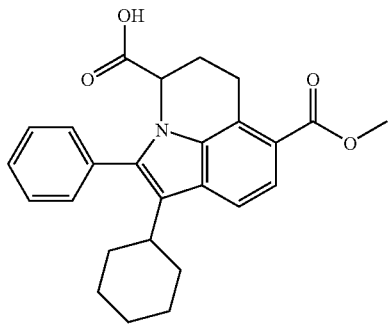

1-cyclohexyl-5,6-dihydro-2-phenyl-4H-pyrrolo[3,2,1-ij]quinoline-4,7-dicarboxylic acid, 7-methyl ester. To the dimethyl ester (4H-pyrrolo[3,2,1-ij]quinoline-4,7-dicarboxylic acid, 1-cyclohexyl-5,6-dihydro-2-phenyl-, dimethyl ester) (61.5 mg, 0.143 mmol) in anround-bottom flask at r.t. under N2 was added a THF (1.5 ml) of TMSOK (25 mg, 0.175 mmol, 90% tech.) and the reaction mixture slowly stirred for 17 hr. The mixture was acidified with hydrochloric acid (1N), and then evaporated. The residue was titurated with water (about 2 ml), and the aqueous mixture decanted. This step was performed three times. After drying, the residue was purified by Biotage flash chromatography (gradient elution, 0 to 30% MeOH/CH$_2$Cl$_2$) to gave the acid product (4H-pyrrolo[3,2,1-ij]quinoline-4,7-dicarboxylic acid, 1-cyclohexyl-5,6-dihydro-2-phenyl-, 7-methyl ester) (34.6 mg, 58%). $^1$H NMR (300 MHz): (CD$_3$OD) δ 7.69 (d, J=8.6, 1H), 7.63 (d, J=8.6, 1H), 7.49 (b s, 3H), 7.39-7.37 (b m, 2H), 4.74 (b d, 1H), 3.90 (s, 3H), 3.74-3.68 (b d, 1H), 2.98 (b m, 1H), 2.69-2.61 (b overlapping m, 2H), 2.25 (b m, 1H), 1.96-1.72 (b overlapping m, 7H), 1.37-1.22 (b m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=418.13, HPLC R$_t$=2.010 min.

EXAMPLE 7

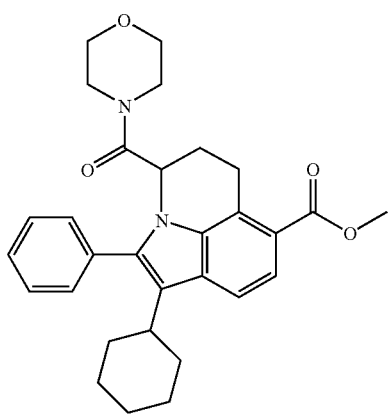

1-cyclohexyl-5,6-dihydro-4-(4-morpholinylcarbonyl)-2-phenyl-4H-pyrrolo[3,2,1-ij]quinoline-7-carboxylic acid, methyl ester. To a mixture of the acid (4H-pyrrolo[3,2,1-ij]quinoline-4,7-dicarboxylic acid, 1-cyclohexyl-5,6-dihydro-2-phenyl-, 7-methyl ester) (33.1 mg, 79.3 μmol) in CH$_2$Cl$_2$ (1 ml) at r.t. under N$_2$ was added a CH$_2$Cl$_2$ solution of oxlyl chloride (0.16 ml, 0.32 mmol, 2M) and DMF (2 drops using a syringe with G21 needle). The reaction was stirred for 2 hr, and then the volatiles were evaporated. The residue was added a CH$_2$Cl$_2$ (1 ml) solution of morpholine (41.5 mg, 0.48 mmol), and stirred at r.t. for 1.5 hr. The crude reacture was then purified by Biotage flash chromatography (50% EtOAc/Hexane) to gave the amide (4H-pyrrolo[3,2,1-ij]quinoline-7-carboxylic acid, 1-cyclohexyl-5,6-dihydro-4-(4-morpholinylcarbonyl)-2-phenyl-, methyl ester) as a yellow solid (31.8 mg, 82%). $^1$H NMR (300 MHz): (CD$_3$OD—CDCl$_3$) δ 7.69 (d, J=8.7, 1H), 7.62 (d, J=8.7, 1H), 7.54-7.52 (b m, 3H), 7.34 (very b s, 2H), 5.18 (b m, 1H), 3.90 (s, 3H), 3.75-3.27 (overlapping m, 8H), 3.20-3.10 (b m, 1H), 3.01 (m, 1H), 2.65 (m, 1H), 2.30-2.25 (b m, 2H), 1.91-1.71 (b overlapping m, 7H), 1.32-1.24 (b m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=487.18, HPLC R$_t$=1.958 min.

The following compounds were prepared in a similar manner as above (Analytical HPLC, LC/MS method same as above).

EXAMPLE 8

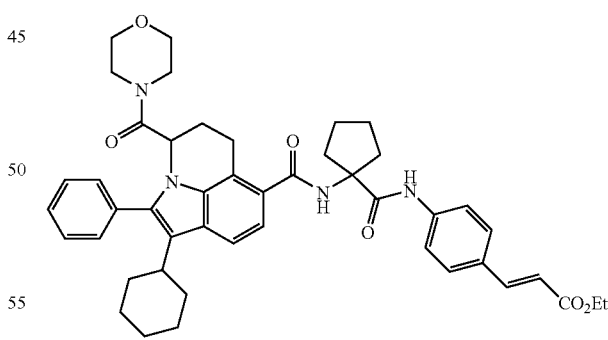

(2E)-3-[4-[[[1-[[[1-cyclohexyl-5,6-dihydro-4-(4-morpholinylcarbonyl)-2-phenyl-4H-pyrrolo[3,2,1-ij]quinolin-7- yl]carbonyl]amino]cyclopentyl]carbonyl]amino]phenyl]-2-propenoic acid, ethyl ester. LC/MS: (ES+) m/z (M+H)$^+$= 757.46, HPLC R$_t$=2.032 min.

EXAMPLE 9

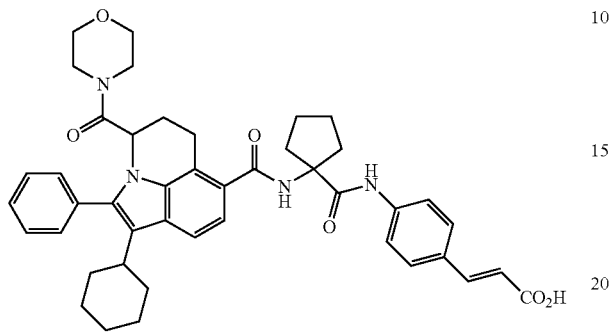

(2E)-3-[4-[[[1-[[[1-cyclohexyl-5,6-dihydro-4-(4-morpholinylcarbonyl)-2-phenyl-4H-pyrrolo[3,2,1-ij]quinolin-7-yl]carbonyl]amino]cyclopentyl]carbonyl]amino]phenyl]-2-propenoic acid. LC/MS: (ES+) m/z (M+H)$^+$=729.40, HPLC R$_t$=1.903 min.

EXAMPLE 10

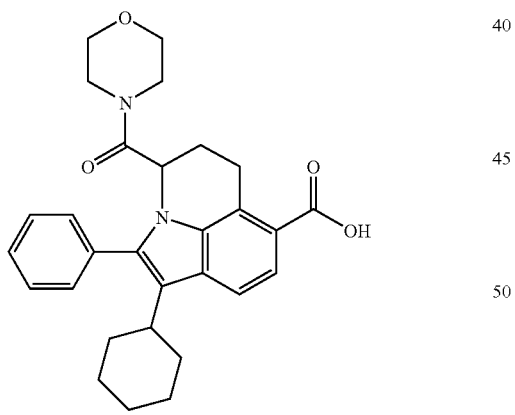

1-cyclohexyl-5,6-dihydro-4-(4-morpholinylcarbonyl)-2-phenyl-4H-pyrrolo[3,2,1-ij]quinoline-7-carboxylic acid. $^1$H NMR (300 MHz): (CD$_3$OD) δ 7.72 (d, J=8.4, 1H), 7.62 (d, J=8.4, 1H), 7.55-7.53 (m, 3H), 7.50-7.20 (very b m, 2H), 5.21 (m, 1H), 3.85-3.30 (overlapping m, 8H), 3.20-3.10 (b m, 1H), 3.00 (m, 1H), 2.66 (m, 1H), 2.35-2.20 (b m, 2H), 2.00-1.60 (b overlapping m, 7H), 1.42-1.24 (b m, 3H); LC/MS: (ES+) m/z (M+H)$^+$=473.20, HPLC R$_t$=1.855 min.

EXAMPLE 11

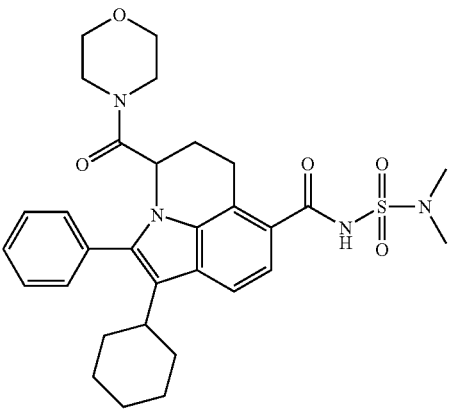

1-cyclohexyl-N-[(dimethylamino)sulfonyl]-5,6-dihydro-4-(4-morpholinylcarbonyl)-2-phenyl-4H-pyrrolo[3,2,1-ij]quinoline-7-carboxamide. LC/MS: (ES+) m/z (M+H)$^+$= 579.35, HPLC R$_t$=1.772 min.

EXAMPLE 12

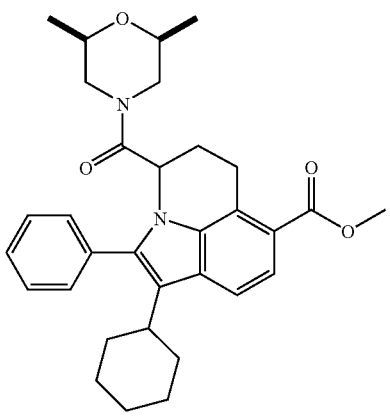

1-cyclohexyl-4-[[(2R,6S)-2,6-dimethyl-4-morpholinyl] carbonyl]-5,6-dihydro-2-phenyl-4H-pyrrolo[3,2,1-ij]quinoline-7-carboxylic acid, methyl ester. LC/MS: (ES+) m/z (M+H)$^+$=515.26, HPLC R$_t$=2.047 min.

EXAMPLE 13

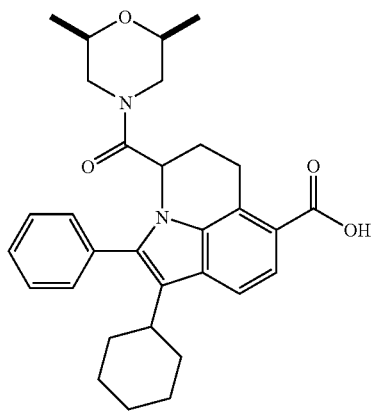

1-cyclohexyl-4-[[(2R,6S)-2,6-dimethyl-4-morpholinyl] carbonyl]-5,6-dihydro-2-phenyl-4H-pyrrolo[3,2,1-ij]quinoline-7-carboxylic acid. LC/MS: (ES+) m/z (M+H)$^+$=501.27, HPLC R$_t$=1.950 min.

EXAMPLE 14

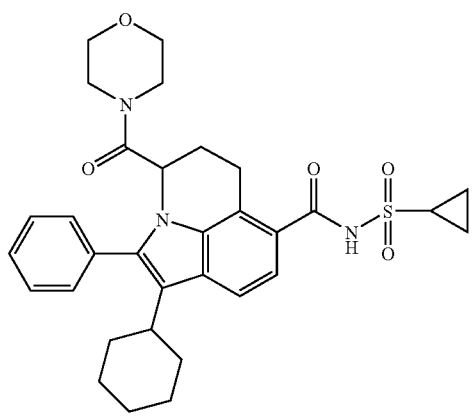

1-cyclohexyl-N-(cyclopropylsulfonyl)-5,6-dihydro-4-(4-morpholinylcarbonyl)-2-phenyl-4H-pyrrolo[3,2,1-ij]quinoline-7-carboxamide. $^1$H NMR (500 MHz): (CD$_3$OD) δ 7.68 (d, J=8.5, 1H), 7.55 (b s, 3H), 7.50-7.20 (very b m, 2H), 7.35 (d overlapping with b m, J=8.5, 1H), 5.23 (dd, J=5.5, 2.5, 1H), 3.60-3.70 (m, 2H), 3.57-3.55 (m, 1H), 3.50-3.39 (overlapping m, 3H), 3.35-3.25 (m overlapping with CD$_3$OD peak, 2H), 3.18-3.12 (overlapping m, 2H), 3.02 (m, 1H), 2.65 (m, 1H), 2.33-2.21 (overlapping m, 2H), 1.96-1.87 (b m, 2H), 1.82-1.81 (b d, 4H), 1.74-1.72 (b d, 1H), 1.38-1.22 (overlapping m, 5H), 1.20-1.10 (overlapping m, 2H); LC/MS: (ES+) m/z (M+H)$^+$=576.27, HPLC R$_t$=1.785 min.

EXAMPLE 15

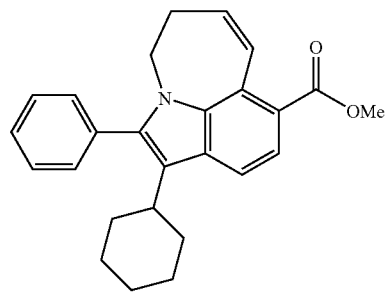

((Z)-methyl 7-cyclohexyl-6-phenyl-3,4-dihydroazepino [3,2,1-hi]indole-10-carboxylate. To a mixture of the vinylindole (1H-indole-6-carboxylic acid, 3-cyclohexyl-7-ethenyl-2-phenyl-, methyl ester) (24 mg, about 66.8 μmol) in DMF (0.8 ml) at r.t. under N$_2$ was added NaH (8.6 mg, 215 μmol, 60% oil), and the mixture stirred for about 5 min. The mixture was then added with a solution of 4-bromo-1-butene (19.7 mg, 146 μmol) in DMF (0.2 ml) and stirred for 20.5 hr. Another batch of NaH (8.6 mg, 215 μmol, 60% oil) followed by another solution of 4-bromo-1-butene (19.7 mg, 146 μmol) in DMF (0.2 ml) were added to the reaction mixture, which was then stirred for another 5 hr. The mixture was concentrated, added with water (2 ml), acidified with hydrochloric acid (1N) and further diluted with water (about 6 ml). The mixture was extracted with CH$_2$Cl$_2$ (8 ml) and evaporated to give the crude product (methyl 1-(but-3-enyl)-3-cyclohexyl-2-phenyl-7-vinyl-1H-indole-6-carboxylate).
Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=414.20, HPLC R$_t$=2.245 min.

To a mixture of the indole (methyl 1-(but-3-enyl)-3-cyclohexyl-2-phenyl-7-vinyl-1H-indole-6-carboxylate) obtained from above and Grubbs 2nd generation catalyst (7.5 mg, 8.83 μmol) at r.t. under N$_2$ was charged CH$_2$Cl$_2$ (4.5 ml), and the reaction mixture was stirred at 50° C. for 1.5 hr. After cooling to r.t., the mixture was purified by Biotage flash chromatography (gradient elution, 0 to 20% EtOAc/Hexane) to gave the product ((Z)-methyl 7-cyclohexyl-6-phenyl-3,4-dihydroazepino[3,2,1-hi]indole-10-carboxylate) (16.8 mg). $^1$H NMR (500 MHz): (CD$_3$OD—CDCl$_3$) δ 7.70 (d, J=8.3, 1H), 7.55-7.49 (m, 3H), 7.52 (d overlapping with m, J=8.3, 1H), 7.36 (b d overlapping with d, 2H), 7.34 (d, J=11.5, 1H), 6.20 (m, 1H), 3.97-3.95 (m, 2H), 3.93 (s, 3H), 2.71-2.60 (m, 3H), 1.95-1.85 (m, 2H), 1.80-1.71 (overlapping m, 5H), 1.32-1.26 (m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)+=386.19, HPLC R$_t$=2.223 min.

EXAMPLE 16

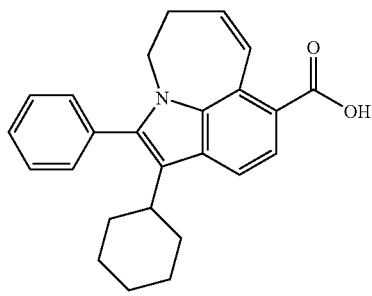

(Z)-7-cyclohexyl-6-phenyl-3,4-dihydroazepino[3,2,1-hi]indole-10-carboxylic acid. To the methyl ester ((Z)-methyl 7-cyclohexyl-6-phenyl-3,4-dihydroazepino[3,2,1-hi]indole-10-carboxylate) (15.9 mg, 41.2 μmol) at r.t. under N$_2$ was added a solution of TMSOK (63.5 mg, 445 μmol, 90% tech.) in THF (1 ml), and the reaction mixture stirred for 17 hr. After concentration, the mixture was washed twice with water (about 1 ml each), and three times with hexane (about 2 ml each) and dried to give the acid ((Z)-7-cyclohexyl-6-phenyl-3,4-dihydroazepino[3,2,1-hi]indole-10-carboxylic acid) (10.2 mg). $^1$H NMR (500 MHz): (CD$_3$OD—CDCl$_3$) δ 7.70 (d, J=8.3, 1H), 7.57-7.43 (m overlapping with two d, 3H), 7.56 (d, J=8.3, 1H), 7.44 (d, J=12, 1H), 7.36-7.35 (b s, 2H), 6.19 (m, 1H), 3.97-3.96 (b d, 2H), 2.70-2.60 (b m, 3H), 1.90-1.62 (b m, 7H), 1.30-1.21 (b s, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)+=372.22, HPLC R$_t$=2.098 min.

EXAMPLE 17

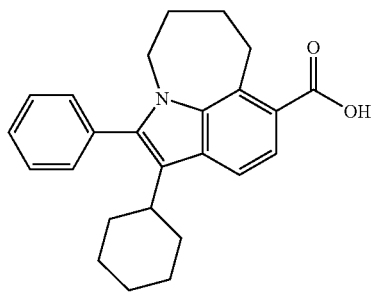

7-cyclohexyl-6-phenyl-1,2,3,4-tetrahydroazepino[3,2,1-hi]indole-10-carboxylic acid. To a mixture of ((Z)-7-cyclohexyl-6-phenyl-3,4-dihydroazepino[3,2,1-hi]indole-10-carboxylic acid) (7.7 mg) in a mixture of EtOAc/EtOH (0.5 ml/0.5 ml) at r.t. under N$_2$ was added Pd/C (10 mg, 10%), and the reaction mixture was stirred under hydrogen gas (using a balloon) for 1.5 hr. The mixture was then diluted with EtOAc, and filtered through a cake of celite. The filtrate was evaporated to give (7-cyclohexyl-6-phenyl-1,2,3,4-tetrahydroazepino[3,2,1-hi]indole-10-carboxylic acid) (7.2 mg). $^1$H NMR (500 MHz): (CD$_3$OD—CDCl$_3$) δ 7.58 (d, J=8.3, 1H), 7.54-7.45 (m overlapping with d, 3H), 7.53 (d, J=8.3, 1H), 7.39-7.36 (m 2H), 3.99 (m, 2H), 3.58 (m, 2H), 2.67 (m, 1H), 2.15 (m, 2H), 2.02 (m, 2H), 1.96-1.89 (b m, 2H), 1.81-1.72 (b overlapping m, 5H), 1.35-1.20 (b m, 3H); Analytical HPLC method: Solvent A=10% MeOH-90% H$_2$O-0.1% TFA, Solvent B=90%, MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)+=374.28, HPLC R$_t$=2.102 min.

EXAMPLE 18

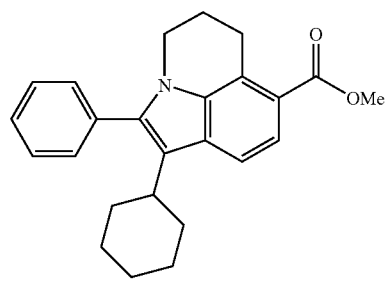

methyl 6-cyclohexyl-5-phenyl-2,3-dihydro-1H-pyrrolo[3,2,1-ij]quinoline-9-carboxylate. Prepared in a similar manner as above. $^1$H NMR (500 MHz): (CD$_3$OD) δ 7.65 (d, J=8.5, 1H), 7.61 (d, J=8.5, 1H), 7.56-7.45 (overlapping m, 3H), 7.43-7.41 (m 2H), 3.93-3.90 (m overlapping with s, 2H), 3.91 (s, 3H), 3.42-3.67 (m, 2H), 2.71 (m, 1H), 2.18 (m, 2H), 2.00-1.93 (b m, 2H), 1.84-1.74 (b overlapping m, 5H), 1.38-1.29 (b m, 3H); Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)+=374.21.

EXAMPLE 19

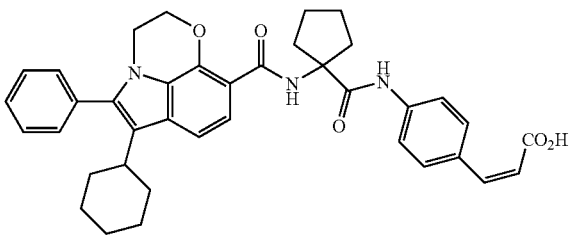

(2Z)-3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-2-propenoic acid. The product was isolated as a side product from the hydrolysis of the ethyl ester 2-propenoic acid, 3-[4-[[[1-[[(6-cyclohexyl-2,3-dihydro-5-phenyl-1,4-oxazino[2,3,4-hi]indol-9-yl)carbonyl]amino]cyclopentyl]carbonyl]amino]phenyl]-, ethyl ester, (2E)-). $^1$H NMR (500 MHz): (CD$_3$OD) δ 7.63 (d, J=8.5, 2H), 7.59-7.50 (overlapping with m, 6H), 7.47 (d, J=8.5, 2H), 7.41 (d, J=8.5, 1H), 6.84 (d, J=13, 1H), 5.91 (d, J=13, 1H), 4.76 (m, 2H), 4.20 (m, 2H), 2.78-2.73 (m, 1H), 2.49-2.46 (b m, 2H), 2.18-2.15 (b m, 2H), 2.01-1.74 (b overlapping m, 10H), 1.40-1.25 (b m, 4H); Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=618.26, HPLC $R_t$=2.035 min.

EXAMPLE 20

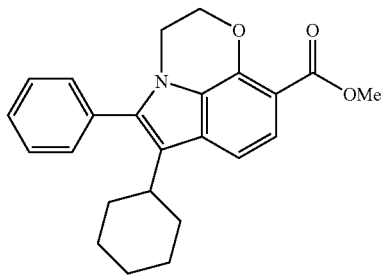

1,4-oxazino[2,3,4-hi]indole-9-carboxylic acid, 6-cyclohexyl-2,3-dihydro-5-phenyl-, methyl ester. The product was also isolated from the cyclization of the alcohol (1H-indole-6-carboxylic acid, 7-chloro-3-cyclohexyl-1-(2-hydroxyethyl)-2-phenyl-, methyl ester) to (1,4-oxazino[2,3,4-hi]indole-9-carboxylic acid, 6-cyclohexyl-2,3-dihydro-5-phenyl-). ¹H NMR (300 MHz): (CD₃OD) δ 7.59-7.44 (d overlapping with m, 6H), 7.34 (d, J=8.7, 1H), 4.57 (t, J=4.8, 2H), 4.11 (t, J=4.8, 2H), 3.90 (s, 3H), 2.80-2.70 (m, 1H), 1.99-1.90 (b m, 2H), 1.85-1.74 (b m, 4H), 1.36-1.31 (b m, 4H); Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=376.17, HPLC $R_t$=2.082 min.

EXAMPLE 21

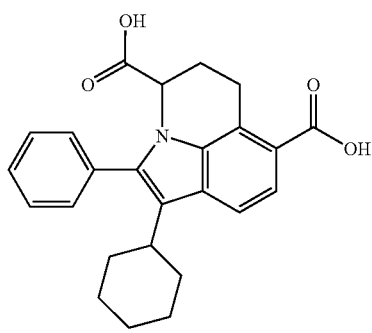

1-cyclohexyl-5,6-dihydro-2-phenyl-H-pyrrolo[3,2,1-ij]quinoline-4,7-dicarboxylic acid. The diacid (H-pyrrolo[3,2,1-ij]quinoline-4,7-dicarboxylic acid, 1-cyclohexyl-5,6-dihydro-2-phenyl-) was obtained from purification of the crude product of the first step (cyclization) during the synthesis of the dimethyl ester (4H-pyrrolo[3,2,1-ij]quinoline-4,7-dicarboxylic acid, 1-cyclohexyl-5,6-dihydro-2-phenyl-, dimethyl ester) from the vinylindole (1H-indole-6-carboxylic acid, 3-cyclohexyl-7-ethenyl-2-phenyl-, methyl ester) by Shimadzu-VP preparative reverse phase HPLC with separation method: Solvent A=10% MeOH-90% H₂O-0.1% TFA, Solvent B=90% MeOH-10% H₂O-0.1% TFA, Start % B=0, Final % B=100, Gradient time=6 min, Flow Rate=30 mL/min, Column: Xterra Prep MS C18 5u 30×50 mm, Fraction Collection: 7.04-7.48 min; Analytical HPLC method: Solvent A 5% MeCN-95% H₂O-10 mM NH₄OAc; Solvent B 95% MeCN-5% H₂O-10 mM NH₄OAc; Start % B=0, Final % B=100, Gradient time=2 min, Flow Rate=5 mL/min, Column: Phenomenex Lina C18 5u 3×50 mm; LC/MS: (ES+) m/z (M+H)⁺=404.55, HPLC $R_t$=0.898.

EXAMPLE 22

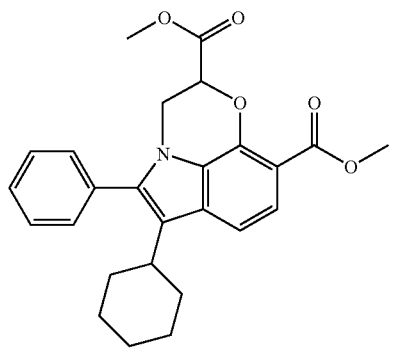

6-cyclohexyl-2,3-dihydro-5-phenyl-1,4-oxazino[2,3,4-hi]indole-2,9-dicarboxylic acid, dimethyl ester. To 1H-indole-6-carboxylic acid, 7-chloro-3-cyclohexyl-2-phenyl-, methyl ester (62 mg, 0.169 mmol) under N₂ at r.t. in a microwave reaction tube was added a solution of methyl (2R)-glycidate (69 mg, 0.676 mmol) in DMSO (1 ml) and NaH (27 mg, 0.675 mmol, 60% in oil), and the reaction mixture stirred at r.t. for 1 hr 25 min. The reaction mixture was then placed under microwave irradiation in an Emrys Optimizer (*Personal Chemistry*) at 200° C. and with the absorption level set to high for 30 min. The mixture was acidified with hydrochloric acid (1N), diluted with water. The brown precipitates were filtered, washed with water twice and then dried. The material was then dissolved in a mixture of benzene/MeOH (1 ml/1 ml), and added with TMSCHN₂ (0.34 ml, 0.68 mmol, 2M in hexane). The reaction was then stirred at r.t. for 2 hr 20 min., quenched with AcOH and the volatiles were evaporated. The residue was purified by Biotage flash chromatography (gradient elution, 0 to 50% EtOAc/Hexane) to gave the dimethyl ester (1,4-oxazino[2,3,4-hi]indole-2,9-dicarboxylic acid, 6-cyclohexyl-2,3-dihydro-5-phenyl-, dimethyl ester). The stereochemical integrity at the α-hydroxyl carbon (C2) was not determined. ¹H NMR (500 MHz): (CD₃OD) δ 7.59-7.56 (overlapping m, 3H), 7.53-7.51 (m, 1H), 7.43 (d, J=8.5, 2H), 7.37 (d, J=8.5, 1H), 5.41 (t, J=3.8, 1H), 4.47 (dd, J=3.8, 12.8, 1H), 4.18 (dd, J=3.8, 12.8, 1H), 3.92 (s, 3H), 3.74 (s, 3H), 2.74 (m, 1H), 1.98-1.75 (b overlapping m, 7H), 1.40-1.31 (b m, 3H); Analytical HPLC method: Solvent A=10% MeOH-90% H₂O-0.1% TFA, Solvent B=90% MeOH-10% H₂O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)⁺=434.15, HPLC $R_t$=2.000 min.

EXAMPLE 23

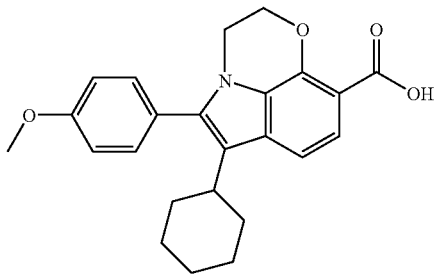

6-Cyclohexyl-5-(4-methoxyphenyl)-2,3-dihydro-[1,4]oxazino[2,3,4-hi]indole-9-carboxylic acid. To a mixture of Methyl-7-chloro-3-cyclohexyl-1-(2-hydroxyethyl)-2-(4-methoxyphenyl)-1H-indole-6-carboxylate (97 mgs, 220 μmol) in 3 mL of anhydrous DMSO, under $N_2$, at room temperature, in a microwave vial, was added 2 equivalents of NaH (95%, 440 μmol, 10.6 mgs). The reaction mixture was stirred for 10 minutes at room temperature then subjected to microwave radiation in a Personal Chemistry Emrys Optimizer™ at 200° C. with the absorption level set to high. The crude product was diluted with 3 mL of HPLC grade acetonitrile and purified by preparative HPLC using the following set of conditions: A Shimadzu UV preparative HPLC employing acetonitrile/water and 10 mM trifluoroacetic acid buffer with a Waters Sunfire, C18, 19 mm×100 mm, 5 μm column with a gradient of 50 to 100% B (B=90% MeCN/10% $H_2O$/0.1% TFA), (A=10% MeCN/90% $H_2O$/0.1% TFA), at a flow rate of 25 mL/min. The purified product, 6-Cyclohexyl-5-(4-methoxyphenyl)-2,3-dihydro-[1,4]oxazino[2,3,4-hi]indole-9-carboxylic acid, was evaporated to dryness to give 15.6 mgs (18%) of a yellow solid. The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 2 minutes with a 1 minute hold at a rate of 5 mL/minute. The NMR spectra was recorded at room temperature using a Bruker DRX300 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). 1H NMR (300 MHz, $CDCl_3$) δ 7.69 (d, J=8.42 Hz, 1H), 7.42 (d, J=8.42 Hz, 1H), 7.29 (d, J=8.78 Hz, 2H), 7.04 (d, J=8.78 Hz, 2H), 4.69 (m, 2H), 4.13 (m, 2H), 3.89 (s, 3H), 2.68 (m, 1H), 1.81 (m, 7H) 1.29 (m, 3H). MS m/z 392.25 (M+H), Rf 2.15 min., 100% purity.

EXAMPLE 24

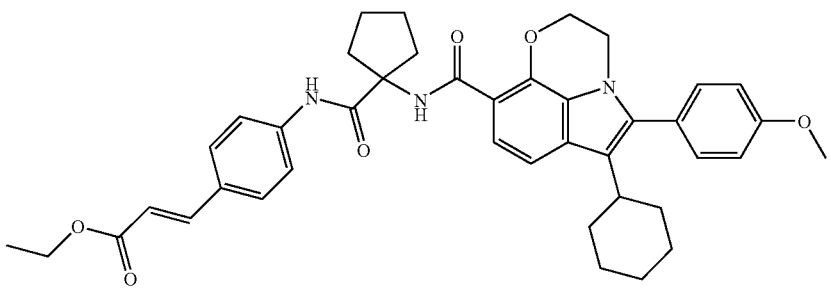

(E)-Ethyl-3-(4-(1-(6-cyclohexyl-5-(4-methoxyphenyl)-2,3-dihydro-[1,4]oxazino[2,3,4-hi]indole-9-carboxamido)cyclopentanecarboxamido)phenyl)acrylate. To 15.6 mgs (40.0 μmol) of indole carboxylic acid was added 2 mL of anhydrous N,N-dimethylformamide (DMF), 3.0 equivalents (120 μmol, 38 mgs) of 2-(1H-benzotriazole-1-yl)-1,1,3,3-tetramethyluronium tetrafluoroborate (TBTU), 2 equivalents (80.0 μmol, 14 μL) of N,N-Diisopropylethyl amine and 2 equivalents (80.0 μmol, 24 mgs) of (E)-1-amino-N-(4-(3-oxopent-1-enyl)phenyl)cyclopentane carboxamide. The mixture was stirred overnight at room temperature. The crude product was dilute with 2 mL of HPLC grade methanol and purified by preparative HPLC using the following set of conditions: A Shimadzu UV preparative HPLC employing methanol/water and 10 mM trifluoroacetic acid buffer with a Phenomenex Luna, C18, 30 mm×50 mm, 10 μm column with a gradient of 50 to 100% B (B=90% MeOH/10% $H_2O$/0.1% TFA), (A=10% MeOH/90% $H_2O$/0.1% TFA), at a flow rate of 40 mL/min. The purified product, (E)-Ethyl 3-(4-(1-(6-cyclohexyl-5-(4-methoxyphenyl)-2,3-dihydro-[1,4]oxazino[2,3,4-hi]indole-9-carboxamido)cyclopentanecarboxamido)phenyl)acrylate, was evaporated to dryness to give 19.6 mgs (65%) of an orange solid. The LC/MS data was obtained on a Shimadzu analytical LC/Micromass Platform LC (ESI+) at 220 nm using the following set of conditions: Phenomenex 10

μm C18, 4.6×30 mm column, with a gradient of 0-100% B (B=90% HPLC grade methanol/0.1% trifluoroacetic acid/ 10% HPLC grade water), (A=90% HPLC grade water/0.1% trifluoroacetic acid/10% HPLC grade methanol), in 2 minutes with a 1 minute hold at a rate of 5 mL/minute. The NMR spectra was recorded at room temperature using a Bruker DRX500 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). 1H NMR (500 MHz, CDCl$_3$) δ 8.08 (d, J=8.24 Hz, 2H), 7.78 (d, J=8.24 Hz, 2H), 7.62 (m, 2H), 7.46 (d, J=8.24 Hz, 1H), 7.28 (d, J=8.54 Hz, 2H), 7.03 (d, J=8.54 Hz, 2H), 6.34 (d, J=15.87, 1H), 4.65 (m, 2H), 4.24 (m, 2H), 4.12 (m, 2H), 3.88 (s, 3H), 2.72 (m, 1H), 2.52 (m, 2H), 2.24 (m, 2H), 1.90 (m, 2H), 1.84 (m, 8H), 1.32 (m, 7H). MS m/z 676.43 (M+H), Rf 2.29 min., 100% purity.

EXAMPLES 25 AND 26

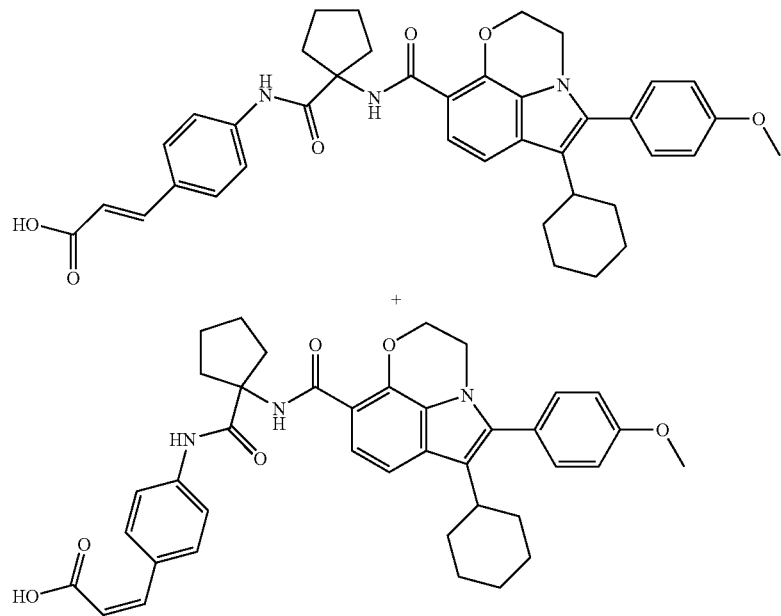

3-(4-(1-(6-cyclohexyl-5-(4-methoxyphenyl)-2,3-dihydro-[1,4]oxazino[2,3,4-hi]indole-9-carboxamido)cyclopentanecarboxamido)phenyl)acrylic acid. To 10.9 mgs (16 μmol) of (E)-Ethyl-3-(4-(1-(6-cyclohexyl-5-(4-methoxyphenyl)-2,3-dihydro-[1,4]oxazino[2,3,4-hi]indole-9-carboxamido)cyclopentanecarboxamido)phenyl)acrylate, in a 2 dram vial, was added 1 mL of anhydrous tetrahydrofuran and 3 equivalents (48 μmol, 6.2 mgs) of potassium trimethylsilanolate (TMSOK). The mixture was stirred overnight at room temperature. The product was concentrated en vacuo, diluted with 2 mL of HPLC grade acetonitrile and purified by preparative HPLC using the following set of conditions: A Shimadzu UV preparative HPLC employing acetonitrile/water and 10 mM trifluoroacetic acid buffer with a Waters Sunfire, C18, 19 mm×100 mm, 5 μm column with a gradient of 30 to 100% B (B=90% MeCN/10% H$_2$O/0.1% TFA), (A=10% MeCN/90% H$_2$O/0.1% TFA) at a flow rate of 25 mL/min. The purified product, 3-(4-(1-(6-cyclohexyl-5-(4-methoxyphenyl)-2,3-dihydro-[1,4]oxazino[2,3,4-hi]indole-9-carboxamido)cyclopentanecarboxamido)phenyl)acrylic acid, was evaporated to dryness to give 2.4 mgs (23%) of a yellow solid that was found to be most likely a mixture of cis/trans isomers based upon the NMR data. The LC/MS data was obtained on a Shimadzu analytical LC/Micromass Platform LC (ESI+) at 220 nm using the following set of conditions: Phenomenex 10 μm C18, 4.6×30 mm column, with a gradient of 0-100% B (B=90% HPLC grade methanol/0.1% trifluoroacetic acid/ 10% HPLC grade water), (A=90% HPLC grade water/0.1% trifluoroacetic acid/10% HPLC grade methanol), in 2 minutes with a 1 minute hold at a rate of 5 mL/minute. The NMR spectra was recorded at room temperature using a Bruker DRX500 spectrometer. Chemical shifts were reported in ppm relative to the deuterated solvent used. Coupling constants were reported in hertz. Peak multiplicity was reported using the following abbreviations: s (singlet), d (doublet), dd (doublet of doublets), t (triplet), m (multiplet), br (broad). 1H NMR (500 MHz, CDCl$_3$) δ 7.98 (d, J=5.80 Hz, 1H), 7.77 (dd, J=8.54 Hz, 2.75 Hz, 1H), 7.72 (d, J=15.87, 0.5H), 7.59-7.66 (m, 2H), 7.49 (d, J=8.54 Hz, 1H), 7.44 (m, 1H), 7.28 (d, J=8.54 Hz, 2H), 7.03 (d, J=8.54 Hz, 2H), 6.98 (d, J=12.51 Hz, 0.5H), 6.35 (d, J=15.87 Hz, 0.5H), 5.87 (d, J=12.51 Hz, 0.5H), 4.63 (m, 2H), 4.10 (m, 2H), 3.89 (s, 3H), 2.68 (m, 1H), 2.53 (m, 2H), 2.25 (m, 2H), 1.80 (m, 10H), 1.29 (m, 4H). MS m/z 648.15 (M+H), Rf 2.19 min., 100% purity.

We claim:
1. A compound of formula I

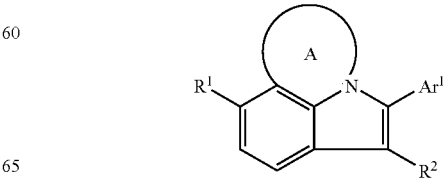

wherein:
   A is a 6-membered ring with 1 O atom and contains 0 double bonds, and is substituted with 0-1 substituents selected from $COR^3$ and $CONR^9R^{10}$;
   $R^1$ is $CO_2R^3$ or $CONR^4R^5$;
   $R^2$ is $C_{5-7}$cycloalkyl;
   $R^3$ is hydrogen or alkyl;
   $R^4$ is hydrogen, alkyl, cycloalkyl, $SO_2R^6$, or

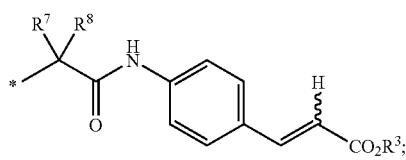

$R^5$ is hydrogen, alkyl, or cycloalkyl;
   $R^6$ is alkyl, haloalkyl, cycloalkyl, amino, alkylamino, or dialkylamino;
   or $R^6$ is pyrrolidinyl, piperidinyl, piperazinyl, homomorpholinyl, homopiperidinyl, morpholinyl, or thiomorpholinyl, and is substituted with 0-2 substituents selected from halo and $C_{1-6}$alkyl;
   $R^7$ and $R^8$ are independently hydrogen or alkyl;
   or $R^7$ and $R^8$ taken together are ethylene, propylene, butylene, pentylene, or hexylene;
   $R^9$ is hydrogen, alkyl, cycloalkyl, hydroxyalkyl, (alkoxy)alkyl, aminoalkyl, (alkylamino)alkyl, or (dialkylamino)alkyl;
   $R^{10}$ is hydrogen, alkyl, cycloalkyl, hydroxyalkyl, (alkoxy)alkyl, aminoalkyl, (alkylamino)alkyl, or (dialkylamino)alkyl;
   or $NR^9R^{10}$ taken together is pyrrolidinyl, piperidinyl, piperazinyl, homomorpholinyl, homopiperidinyl, morpholinyl, or thiomorpholinyl, and is substituted with 0-2 substituents selected from halo, hydroxy, alkyl, amino, alkylamino, dialkylamino, pyridinyl, pyrrolidinyl, piperidinyl, piperazinyl, N-(alkyl)piperazinyl, morpholinyl, and thiomorpholinyl; and
   $Ar^1$ is phenyl substituted with 0-2 substituents selected from halo, alkyl, and alkoxy;
or a pharmaceutically acceptable salt thereof.

2. A composition comprising a compound of claim 1, or a pharmaceutically acceptable salt thereof, and a pharmaceutically acceptable carrier.

3. A method of treating hepatitis C infection comprising administering a therapeutically effective amount of a compound of claim 1 to a patient.

4. A compound of claim 1 according to the following structure:

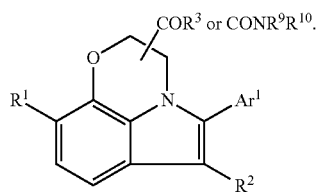

5. A compound of claim 1 according to the following structure:

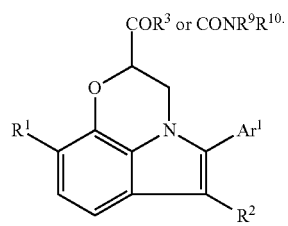

6. A compound of claim 1 according to the following structure:

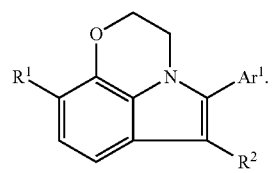

7. A compound of claim 1 selected from the group consisting of

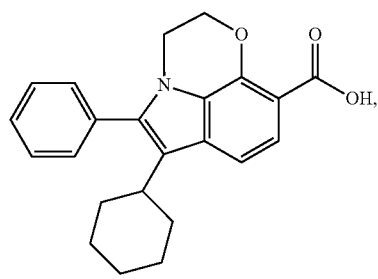

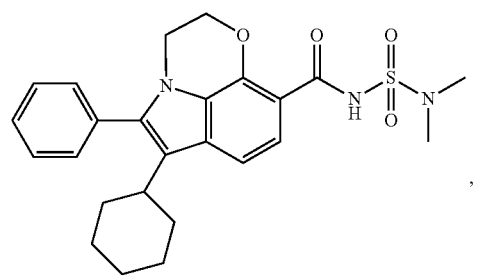

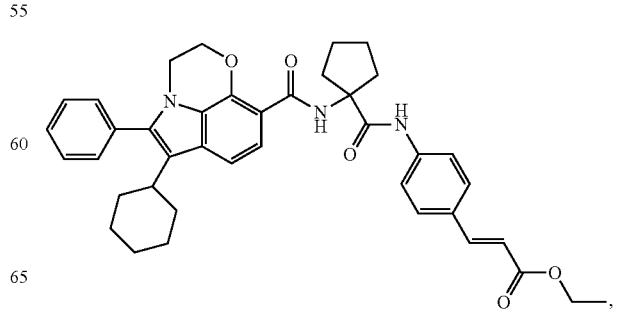

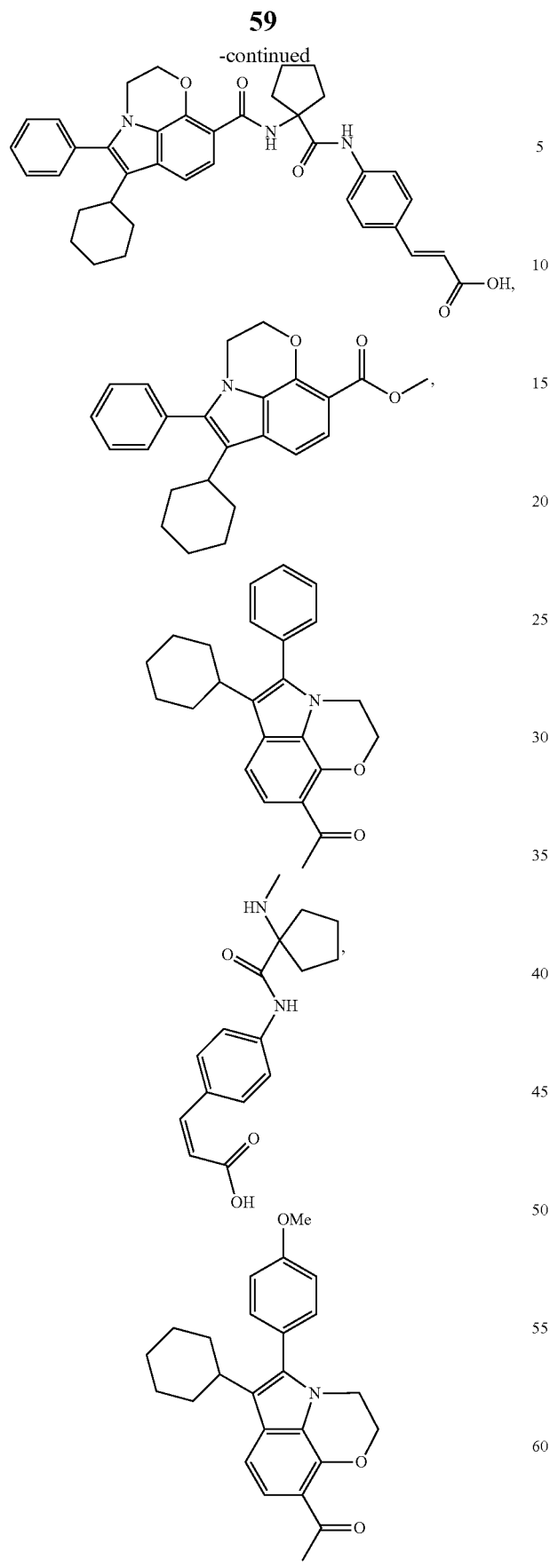
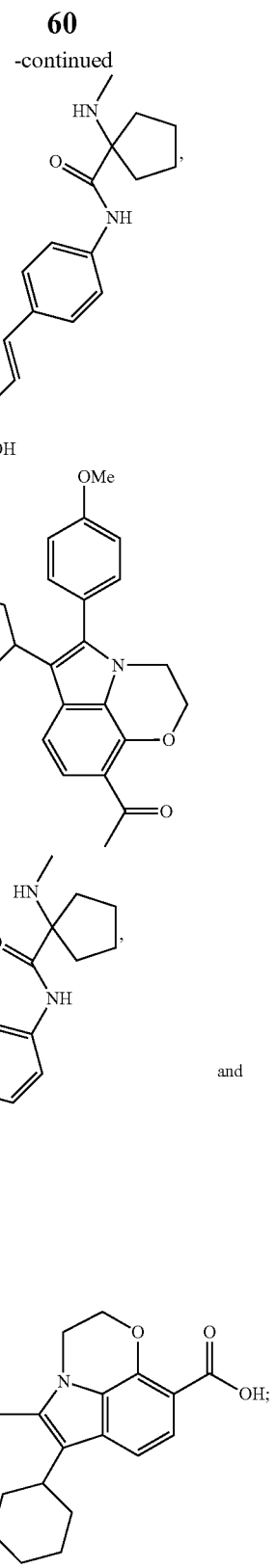
or a pharmaceutically acceptable salt thereof.
* * * * *

UNITED STATES PATENT AND TRADEMARK OFFICE
CERTIFICATE OF CORRECTION

PATENT NO.         : 7,998,951 B2                                              Page 1 of 2
APPLICATION NO.    : 12/041072
DATED              : August 16, 2011
INVENTOR(S)        : Kap-Sun Yeung et al.

It is certified that error appears in the above-identified patent and that said Letters Patent is hereby corrected as shown below:

In the Claims:

Claim 1:
　　　Column 57, line 30, change "hexylene" to -- hexalene --.
Claim 7:
　　　Column 59, lines 23 to 49, change

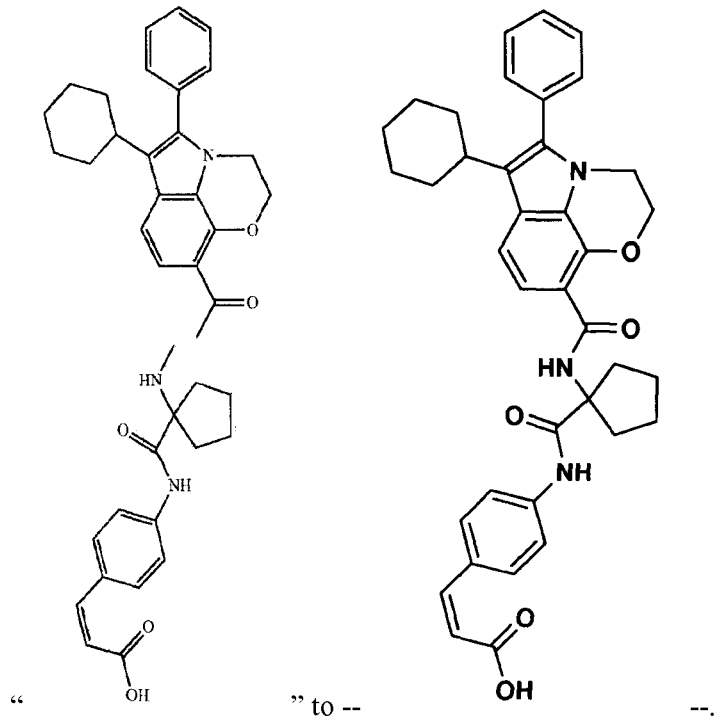

" to -- -- .

Signed and Sealed this
Twentieth Day of December, 2011

David J. Kappos
*Director of the United States Patent and Trademark Office*

CERTIFICATE OF CORRECTION (continued)
U.S. Pat. No. 7,998,951 B2

Claims 7 (continued):
Column 59, lines 50 to 65 and Column 60, lines 1 to 17, change

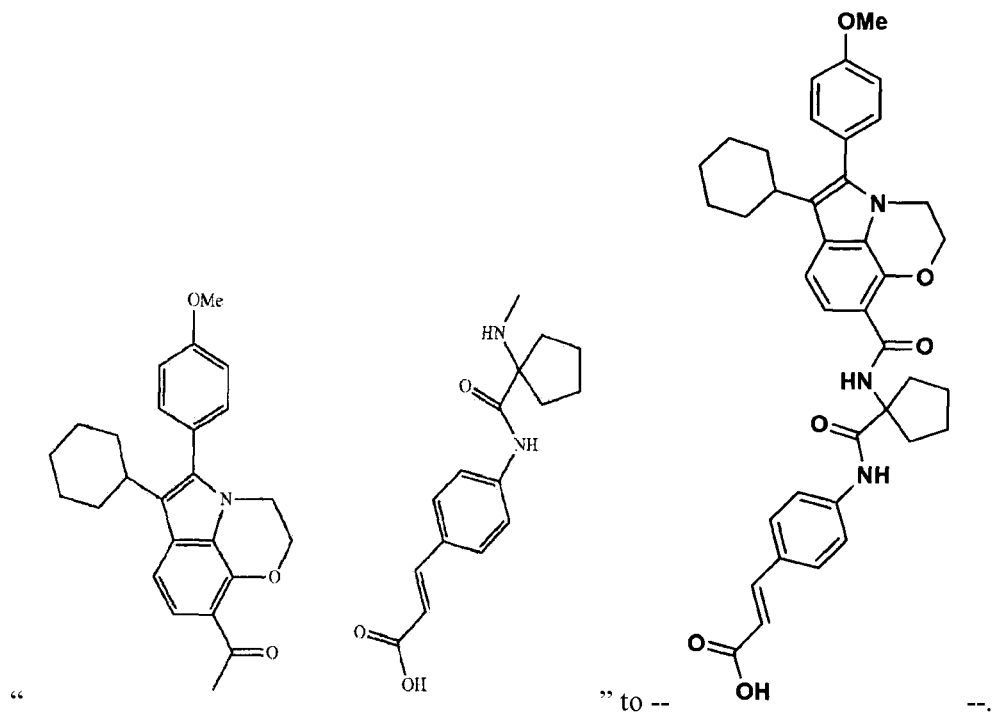

" to -- --.

Column 60, lines 18 to 49, change

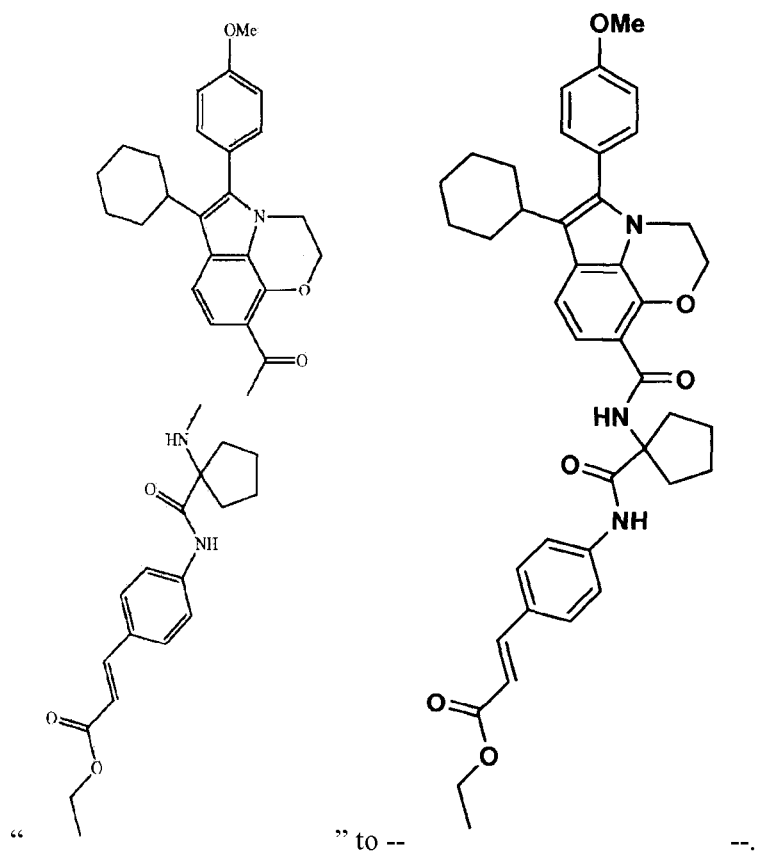

" to -- --.